United States Patent [19]

Kim

[11] Patent Number: 5,698,527
[45] Date of Patent: Dec. 16, 1997

[54] STEROIDAL GLYCOSIDES AS ANTIHYPERLIPIDEMIC AGENTS

[75] Inventor: Dooseop Kim, Westfield, N.J.

[73] Assignee: Merck & Co., Inc., Rahway, N.J.

Related U.S. Application Data

[60] Provisional application No. 60/002,039 Aug. 8, 1995.

[21] Appl. No.: 688,582

[22] Filed: Jul. 30, 1996

[51] Int. Cl.$^6$ .................................................. A61K 31/705
[52] U.S. Cl. .................................................. 514/26; 536/5
[58] Field of Search ................................ 514/26; 536/5

[56] References Cited

U.S. PATENT DOCUMENTS

| 4,602,003 | 7/1986 | Malinow | 514/26 |
|---|---|---|---|
| 4,602,005 | 7/1986 | Malinow | 514/26 |
| 5,041,541 | 8/1991 | Mazur | 536/11 |

FOREIGN PATENT DOCUMENTS

| WO 94/00480 | 1/1994 | WIPO . |
|---|---|---|
| WO 94/05152 | 3/1994 | WIPO . |
| WO 95/18143 | 7/1995 | WIPO . |
| WO 95/18144 | 7/1995 | WIPO . |

OTHER PUBLICATIONS

Harwood et al., J. of Lipid Res., vol. 32 (1993), pp. 377–395, "Pharmacologic consequences of cholesterol absorption inhibition: alteration in cholesterol metabolism and reduction...".

Melchoir et al., J. of Lipid Res., vol. 26 (1985), pp. 306–315, "Cholesterol absorption and turnover in hypercholesterolemic dogs".

Holman et al., Lab. Invet., vol. 7 (1958), pp. 42–47, "Technics for studying athersclerotic lesions".

*Primary Examiner*—Amelia Owens
*Attorney, Agent, or Firm*—Carol S Quagliato; Melvin Winokur

[57] ABSTRACT

Ergostanone derivatives substituted with dissaccharides are cholesterol absorption inhibitors useful in the treatment of hypercholesterolemia and related disorders. These cholesterol absorption inhibitors may be employed alone or in combination with other cholesterol lowering agents.

13 Claims, No Drawings

STEROIDAL GLYCOSIDES AS ANTIHYPERLIPIDEMIC AGENTS

This is a continuation of provisional application 06/002,039 filed Aug. 8, 1995.

BACKGROUND OF THE INVENTION

Hypercholesterolemia is one of the prime risk factors for ischemic cardiovascular disease, such as arteriosclerosis and atherosclerosis. Many patients suffering from hypercholesterolemia cannot adequately lower their cholesterol levels with diet.

Bile acid sequesterants have been used to treat this condition; these cross-linked synthetic polymer derivatives are moderately effective, but they must be consumed in large quantities (i.e. several grams at a time), are not very palatable, and can cause mild gastric distress thus resulting in poor patient compliance. Moreover, bile acid sequesterants can interfere with the bioavailability of several medications in patients receiving concurrent therapy.

MEVACOR® (lovastatin), ZOCOR® (simvastatin), PRAVACHOL® (pravastatin) and LESCOL® (fluvastatin), now commercially available, are members of a group of very active antihypercholesterolemic agents that function by lowering cholesterol biosynthesis by inhibiting the enzyme HMG-CoA reductase.

Other known hypercholesterolemia controlling agents include plant extracts such as "alfalfa saponins" which function, in part, by blocking cholesterol absorption in the gut. These plant extracts contain significant amount of nonuseful chemical substances which have the potential to block the absorption of lipophillic nutrients and may prove harmful after dosing over an extended period of time. Thus, such extracts are not well suited for use by humans. Additionally, the pure sapogenin components, unless administered in massive amounts, do not significantly inhibit cholesterol's absorption. Examples of such sapogenin compounds are tigogenin and diosgenin. Alternatively, certain synthetically produced, pure "sapogenin-derived" compounds such as b-tigogenin cellobioside inhibits cholesterol absorption more effectively and specifically than alfalfa extracts or sapogenins on a weight basis and thus can be administered in more reasonably sized doses (J. H. Harwood et al.; Journal of Lipid Research, Vol. 32, pp 377, (1993)). In addition pure compounds of this nature have the capacity to specifically inhibit dietary and biliary cholesterol absorption while having little effect on bile acid and vitamin absorption. U.S. Pat. Nos. 4,602,003 and 4,602,005 and WO 94/00480 disclose certain steroidal glycosides, 3-O-(β-D-cellobiosyl)tigogenin and 3-O-(β-D-cellobiosyl)-11-ketotigogenin and their use for the control of hypercholesterolemia. 3-O-(β-D-cellobiosyl)tigogenin has superior hypocholesterolemic activity when compared to, for example, cholestyramine.

Although the hypocholesterolemic compounds described above make a significant contribution to the art, there is a continuing search in this field of art for improved hypocholesterolemic pharmaceuticals.

SUMMARY OF THE INVENTION

Steroidal derivatives of formula I are novel cholesterol absorption inhibitors and are useful in the treatment of hypercholesterolemia.

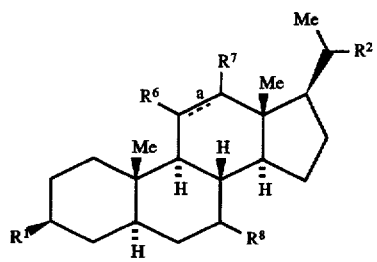

The compounds are also useful in the treatment of disorders associated with hypercholesterolemia, for example atherosclerosis, particularly arteriosclerosis, and for the prevention of coronary artery disease. These cholesterol absorption inhibitors may be employed alone or in combination with other cholesterol lowering agents. Processes for making the compounds of the present invention are also disclosed. The present invention also comprises novel pharmaceutical compositions comprising the novel steroidal derivatives of the present invention.

DETAILED DESCRIPTION OF THE INVENTION

The novel cholesterol absorption inhibitors of this invention are compounds of structural formula (I):

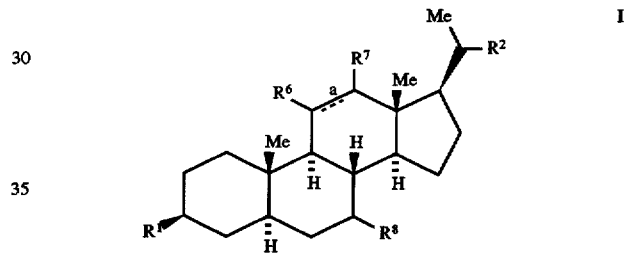

and the pharmaceutically acceptable salts and hydrates thereof wherein:

$R^1$ is selected from:

a) —O—X, b) —O-phenyl substituted at the 3 or 4 position with X, c) -phenyl-4-O—X or β-phenyl-3-O—X, and wherein X is a sugar selected from β-D-cellobiosyl, β-D-glucopyranosyl, β-D-galactopyranosyl, β-D-2-acetamido-2-deoxy-glucopyranosyl, β-D-fucopyranosyl, β-D-maltosyl, β-D-lactosyl, β-D-cellotriosyl and β-D-maltotriosyl;

$R^2$ is selected from:

a) —$C_1$–$C_8$-alkyl, —$C_3$–$C_8$ alkenyl or -$C_3$–$C_7$-cycloalkyl unsubstituted or wherein each may be substituted with one to three substituents selected from: halogen, —O—$C_1$–$C_4$ alkyl, aryl, heteroaryl, O-aryl and O-heteroaryl, b) aryl, c) heteroaryl, d) —$CH_2OC(O)NH$—$R^3$, e) —$CH_2O(CO)NH$—$SO_2$—$R^3$, f) —$CH_2OC(O)$—$R^3$, g) —$OR^3$, h) —$OC(O)NH$—$R^3$, i) —$O(CO)NH$—$SO_2$—$R^3$, j) —$OC(O)$—$R^3$, k) —$CH_2$—$NR^3R^4$, l) —CH$_2$NHC(O)R$^3$,
m) —CH$_2$NHC(O)OR$^3$,
n) —CH$_2$NHC(O)NHR$^3$,
o) —NR$^3$R$^4$,
p) —NHC(O)R$^3$,
q) —NHC(O)OR$^3$,
r) —NHC(O)NHR$^3$,
s) —C(O)R$^3$,
t) —CO$_2$-t-Bu,
u) —CONR$^3$R$^4$,
v) —CH=CR$^3$R$^4$,
w)

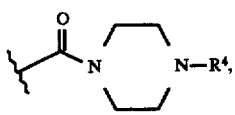

x)

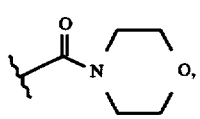

y)

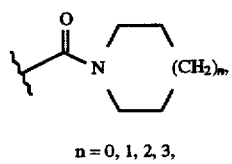

n = 0, 1, 2, 3, and z)

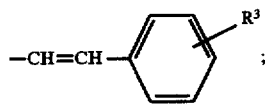

R$^3$ and R$^4$ are independently selected from:
a) —H,
b) C$_1$–C$_{10}$-alkyl, C$_3$–C$_{10}$ alkenyl or C$_3$–C$_{10}$-cycloalkyl, unsubstituted or wherein each may be substituted with one to three substituents selected from:
  1) halogen
  2) —O—C$_1$–C$_4$ alkyl,
  3) aryl,
  4) heteroaryl,
  5) =O,
  6) —C(O)-aryl,
  7) —C(O)—C$_1$–C$_{10}$ alkyl,
  8) —C(O)O-aryl,
  9) —C(O)O—C$_1$–C$_{10}$ alkyl,
  10) —C(O)NH-aryl,
  11) —C(O)NH—C$_1$–C$_{10}$ alkyl,
  12) —N(R$^5$)$_2$, wherein R$^5$ is independently selected at each occurrence from the group: —H, —C$_1$–C$_{10}$ alkyl, —C$_3$–C$_{10}$ alkenyl, —C$_3$–C$_{10}$ cycloalkyl, aryl and heteroaryl;
c) aryl, and
d) heteroaryl;

R$^{3a}$ is selected from:
a) C$_1$–C$_{10}$-alkyl, C$_3$–C$_{10}$ alkenyl or C$_3$–C$_{10}$-cycloalkyl, unsubstituted or wherein each may be substituted with one to three substituents selected from:
  1) halogen
  2) —O—C$_1$–C$_4$ alkyl,
  3) aryl,
  4) heteroaryl,
  5) =O,
  6) —C(O)-aryl,
  7) —C(O)—C$_1$–C$_{10}$ alkyl,
  8) —COO-aryl,
  9) —COO—C$_1$–C$_{10}$ alkyl,
  10) —C(O)NH-aryl,
  11) —C(O)NH—C$_1$–C$_{10}$alkyl,
  12) —N(R$^5$)$_2$, wherein R$^5$ is independently at each occurrence from the group: —H, —C$_1$–C$_{10}$ alkyl, —C$_3$–C$_{10}$ alkenyl, —C$_3$–C$_{10}$ cycloalkyl, aryl and heteroaryl;
b) aryl, and
c) heteroaryl;

R$^6$ and R$^7$ are independently selected from:
a) —H,
b) OH,
c) oxo (=O),
d) =N—OR$^3$,
e) —NR$^3$R$^4$,
f) —NHCOR$^{3a}$,
g) —NHCONR$^3$R$^4$,
h) —NHCO$_2$R$^{3a}$, and
i) —SO$_2$R$^{3a}$;

R$^8$ is selected from:
a) —H and
b) oxo (=O);

the line "---" designated as a represents a single or double bond when R$^6$ and R$^7$ are independently selected from —H and —SO$_2$R$^3$; otherwise, a is a single bond;

aryl is phenyl or bi-phenyl unsubstituted or wherein each may be substituted with one or two substituents selected from the group: halogen (F, Cl, Br, I), OH, NR$^3$R$^4$, CO$_2$R$^3$, C$_1$–C$_4$ alkyl, C$_1$–C$_4$ alkoxy, NO$_2$, CF$_3$, C$_1$–C$_4$ alkylthio, methylenedioxy, SO$_2$—(C$_1$–C$_8$) alkyl, SO$_2$-aryl, and SO$_2$-heteroaryl; and heteroaryl is selected from
(a) an unsubstituted, monosubstituted or disubstituted five or six membered aromatic ring which consists of carbon atoms and from one to three heteroatoms selected from the group O, N and S,
(b) an unsubstituted, monosubstituted or disubstituted eight to ten membered bicyclic ring system which is completely or partially unsaturated and which consists of carbon atoms and from one to three heteroatoms selected from the group O, N, S, and NH;
and wherein the substituents on the heteroaryl are independently selected from the group consisting of halogen, OH, NR$^3$R$^4$, CO$_2$R$^3$, C$_1$–C$_4$ alkyl, C$_1$–C$_4$ alkoxy, NO$_2$, CF$_3$, C$_1$–C$_4$ alkylthio, SO$_2$—(C$_1$–C$_8$) alkyl, SO$_2$-aryl, and SO$_2$-heteroaryl.

In a first embodiment of the present invention are compounds of Formula I wherein X is β-D-cellobiosyl.

In a first class of the first embodiment are compounds further limited to those wherein R$^1$ is β-D-O-cellobiosyl.

This first class of the first embodiment is more particularly limited to compounds wherein R$^3$ is —H and R$^4$ is selected from phenyl; phenyl monosubstituted with halogen; benzyl; and $C_1$–$C_8$ alkyl.

In a second embodiment of the present invention are compounds of Formula I wherein $R^2$ is selected from a) —CH=$CR^3R^4$,
b) —$CH_2$OC(O)NH—$R^3$,
c) —OC(O)NH—$R^3$,
d) —$CH_2$NHC(O)NH$R^3$,
e) —NHC(O)NH$R^3$,
f) —$CH_2$NHC(O)$R^{3a}$,
g) —NHC(O)$R^{3a}$ and
h) —C(O)NH$R^3$.

In a first class of the second embodiment are compounds further limited to those wherein $R^6$ is selected from =O and —$SO_2R^{3a}$; $R^7$ is —H; and $R^8$ is —H.

This first class of the second embodiment is more particularly limited to compounds wherein $R^3$ is selected from:

a) $C_1$–$C_8$ alkyl unsubstituted or substituted with one to three substituents selected from the group consisting of halogen, —$OC_1$–$C_4$ alkyl, aryl and heteroaryl, and
b) aryl.

In a second class of the second embodiment are compounds further limited to those wherein $R^2$ is selected from:

a) —CH=CH—$C_1$–$C_8$ alkyl, and
b) —CH=CH—phenyl, wherein the phenyl is optionally substituted with $C_1$–$C_8$ alkyl; and $R^6$ is selected from =O and —$SO_2R^3$.

This second class of the second embodiment is more particularly limited to compounds wherein $R^6$ is =O; $R^7$ is —H; and $R^8$ is —H.

Examples of compounds of formula I are shown, but are not limited to, those defined in Table I below.

As used herein "alkyl" is intended to include both branched- and straight-chain saturated aliphatic hydrocarbon groups having the specified number of carbon atoms, e.g., methyl (Me), ethyl (Et), propyl, butyl (Bu), pentyl, hexyl, heptyl, octyl, nonyl, decyl and the isomers thereof such as isopropyl (i-Pr), isobutyl (i-Bu), secbutyl (s-Bu), tertbutyl (t-Bu), isopentyl, isohexyl and the like. The term "cycloalky" is intended to include cyclized alkyl chains having the specified number of carbon atoms, e.g., cyclopropyl, cyclobutyl, cyciopentyl, cyclohexyl, cycloheptyl, cyclooctyl, cyclononyl and cyclodecyl. "Alkoxy" represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like. The term "alkenyl" is intended to include both branched- and straight-chain hydrocarbon groups having the specified number of carbon atoms with one or more carbon-carbon double bonds which may occur at any stable point along the chain, e.g., propenyl (allyl), butenyl, pentenyl, hexenyl, heptenyl, octenyl, nonenyl, decenyl, 3,4-dimethyl-1-pentenyl, 4-methyl-pent-2-enyl, and the like. Included in this invention are all E,Z diastereomers.

The term halo or halogen is meant to include fluoro, chloro, bromo and iodo, unless otherwise noted. The term "aryl" is defined above in the definition of Formula I.

The term heteroaryl is defined above in the definition of Formula I. The term heteroaryl encompasses a five or six-membered heteroaryl ting as defined in formula I fused to a benzene, pyridine or pyrimidine ring. The monocyclic and bicyclic heteroaryls described above are unsubstituted, or can be mono- or di-substituted on any available carbon atoms or heteroatom in the ring which results in the creation of a stable structure. The heteroaryl ring may be attached within structural Formula I by any carbon atom or heteroatom, e.g., N, in the ring which results in the creation of a stable structure. Examples of heteroaryl groups include pyrrolyl, triazolyl, pyrazolyl, imidazolyl, pyridinyl, pyrimidinyl, pyrazinyl, furanyl, pyranyl, thiophenyl, oxazolyl, thiazolyl, indolyl, benzimidazolyl, benzofuranyl, benzopyranyl, quinolyl, isoquinolyl and the like. The heteroaryl ring may be attached within structural Formula I at any heteroatom or a carbon atom in the ring which results in the creation of a stable structure.

The compounds of the present invention are chiral and the present compounds may occur as racemates, racemic mixtures and as individual diasteriomers with all such isomeric forms being included within the scope of this invention, except where the stereoconfiguration of a specific chiral center is defined or depicted otherwise. Furthermore, some of the crystalline forms for compounds of the present invention may exist as polymorphs and as such are intended to be included in the present invention. In addition, some of the compounds of the instant invention may form solvates with water or common organic solvents. Such solvates and hydrates are encompassed within the scope of this invention.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g., by reacting the free acid with a suitable organic or inorganic base.

The term "therapeutically effective amount" shall mean that amount of a drug or pharmaceutical agent that will elicit the biological or medical response of a tissue, system, animal or human that is being sought by a researcher, veterinarian, medical doctor or other clinician, which includes alleviation of the symptoms of the disease being treated and the slowing or halting of progression of the condition. The term "mammal" includes humans.

The compounds of the present invention can be prepared readily according to the following Schemes and Examples or modifications thereof using readily available starting materials, reagents and conventional synthesis procedures. Those skilled in the art will readily understand that known variations of the conditions and processes of the following preparative procedures can be used to prepare these compounds. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Specific definitions of variables in the Schemes are illustrative only, and are not intended to limit the procedures described, unless otherwise noted. Some abbreviations used herein are as follows: Ph is phenyl; Ac is an acyl group; Me is methyl; Et is ethyl; Bu is butyl; Bn is benzyl; EtOAc is ethyl acetate; THF is tetrahydrofuran; DMSO is dimethylsulfoxide; TBDMS is t-butyl-dimethyl silyl; TBAF is tetrabutylammonium fluoride; Ts is tosyl; DEAD is dietyl azodicarboxylate; $PPh_3$ is triphenyl phophine. Many of the compounds described in the examples were analyzed by FAB mass spectroscopy (FABMS), and MS values are denoted. Unless otherwise noted, the variables used in the following schemes (i.e., $R^1$, $R^2$, X, etc.) are as defined above in formula I.

Steroids of formula 1 (Scheme 1) are prepared as outlined in the schemes below.

Standard carbohydrate protocols (*Angew. Chem. Int. Ed. Engl.*, 25 (1986) 212–235) are used to couple the steroid with a glycosyl donor (glycosyl-Q, where Q may be Br, F or other leaving groups known to those skilled in the art, and glycosyl is a protected form of the sugars defined in formula I as X; for example, glycosyl-Q may be 1-α-bromo-cellobiosyl heptaacetate), in an aprotic solvent such as acetonitrile, dichloromethane, or toluene in the presence of a Lewis acid such as $ZnF_2$, $ZnBr_2$, $Hg(CN)_2$, $SnCl_4$ or $BF_3$ $Et_2O$, at room temperature (rt) to about 80° C. for about 3 to 18 hours to give the coupled compound 2. Preferably, a glycosyl bromide can be used with $ZnF_2$ in acetonitrile at 70° C. Mild hydrolysis of acyl protecting groups on the glycosyl-portion with sodium methoxide or sodium hydroxide in alcoholic/THF provide the desired compounds.

Starting with $D^{7,9(11),22}$ ergostatrien-3β-ol acetate 3, a versatile intermediate 6 can be synthesized according to the procedures as described in the literatures [*J. Am. Chem. Soc.* 73, (1951), 2396–2398; ibid, 75, (1953), 3477–3483] (Scheme 2A). Diketo derivative 6 can be converted to 7 after hydrolysis, followed by coupling with glycosyl-Q to form 8. Deprotection of the glycosyl group of compound 8, followed by reduction of the double bond at the 22 position using standard hydrogenation methods, for example $H_2$ and Pd/C, gives the final product 13A.

As shown in Scheme 2B, selective reduction of carbonyl at the 7-position of compound 6 using the Wolff-Kishner method [*J. Am. Chem. Soc.* 73, (1951), 2396–2398; ibid, 75, (1953), 3477–3483] can give compound 9 which can be convened to oxime derivative 10 using appropriate reagents such as $NH_2OH$ and pyridine. Reduction of the oxime function to the amine by standard procedures [*J. Org. Chem.* 31 (1966), 1346; ibid, 31, (1966), 1342; *Chem. Ind.* (1972), 683] can give amino derivative 11. Treatment of compound 11 with various acylating agents, acyl halides, chloroformates, isocyanates, sulfonyl isocyanates, and alkylating agents can give compound 12. After deprotection of the 3-OAc group, compound 12 is then coupled to a glycosyl donor, and the glycosyl group is deprotected. Reduction of the double bond at the 22 position can be accomplished as described in scheme 2A, to give compound 13B.

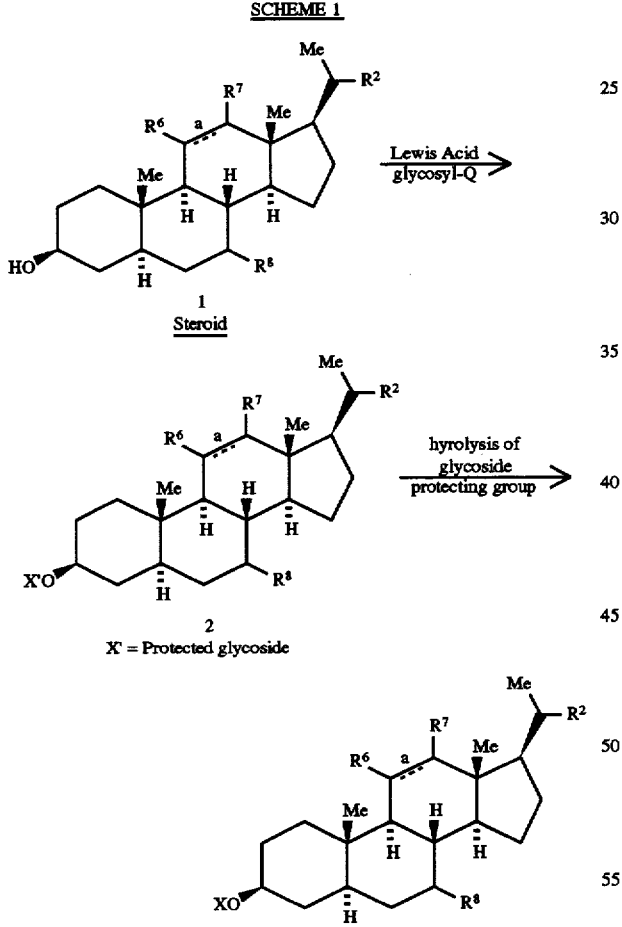

SCHEME 1

SCHEME 2A
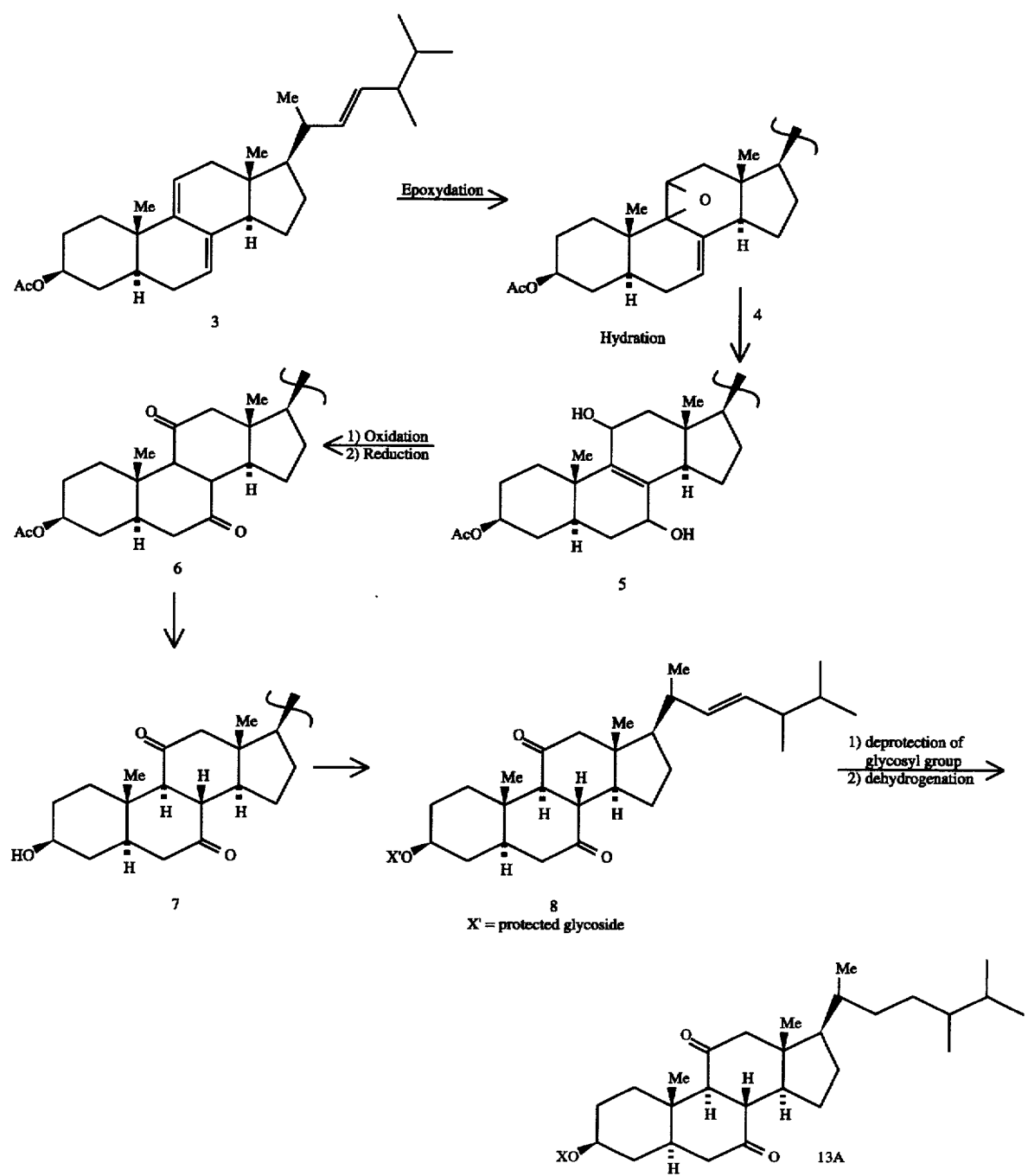

SCHEME 2B

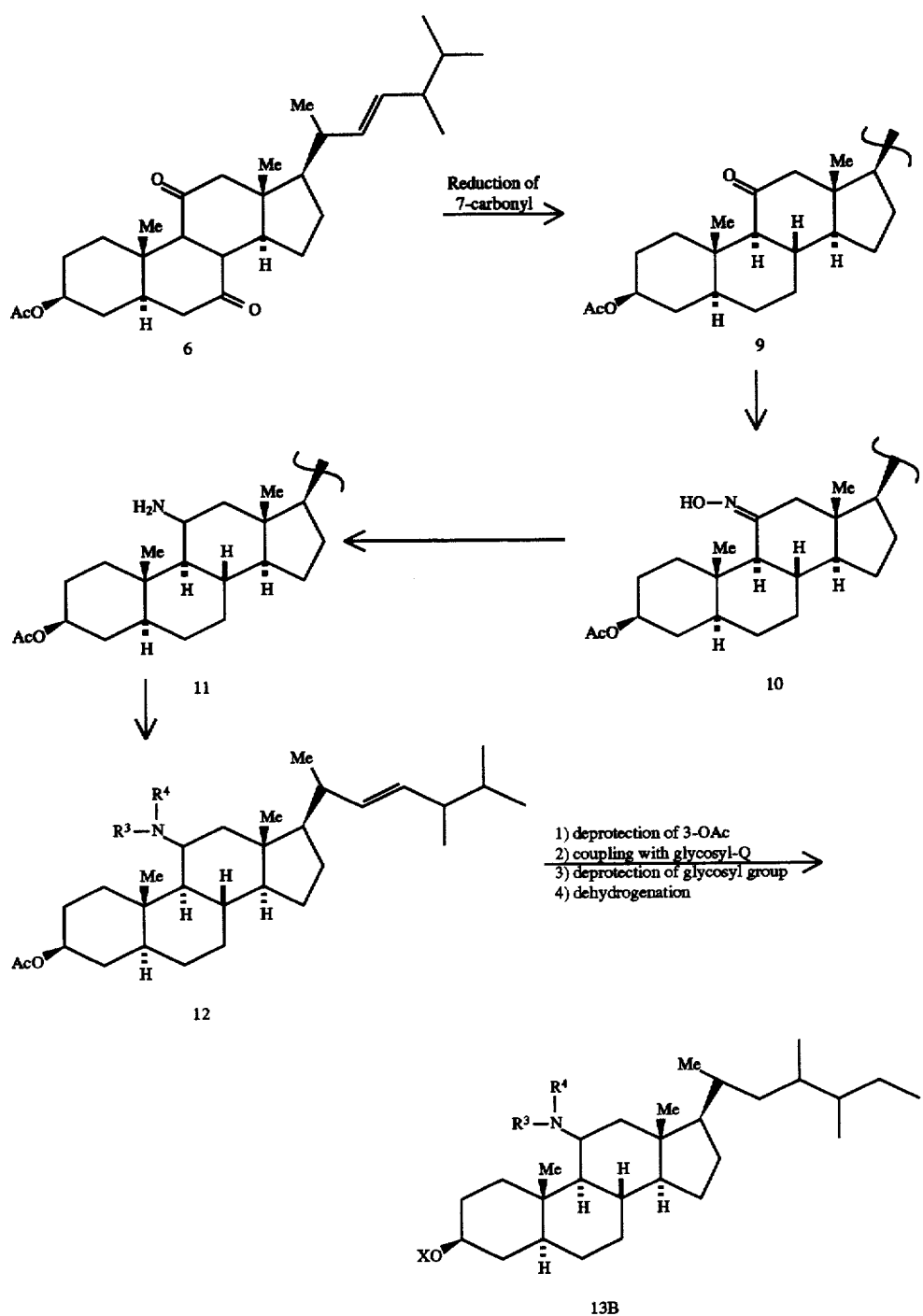

Compound 14, having an olefin side chain, can be converted to a versatile intermediate, aldehyde 15, for the synthesis of various steroid analogs, using standard oxidative cleavage methods, for instance, ozonolysis (Scheme 3). Aldehyde 15 can be further oxidized to carboxylic acid 16 using standard oxidation methods [*J. March in Advanced Organic Chemistry*, Chapter 14, 4th Ed., Wiley Interscience 1992, pp 701–703, and references cited therein; *Tetrahedron Lett.* 27, (1986), 4537–4540]. Carboxylic acid 16 can be converted to acyl halides or activated esters using an appropriate carbodiimide such as EDC, and HOBT to be coupled with various amines ($HNR^3R$). Hydrolysis of the 3-OAc group gives compound 17.

SCHEME 3
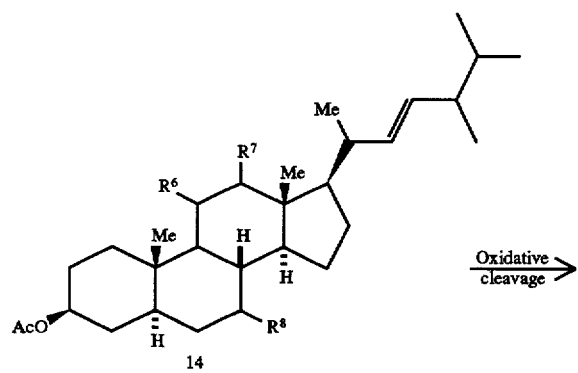
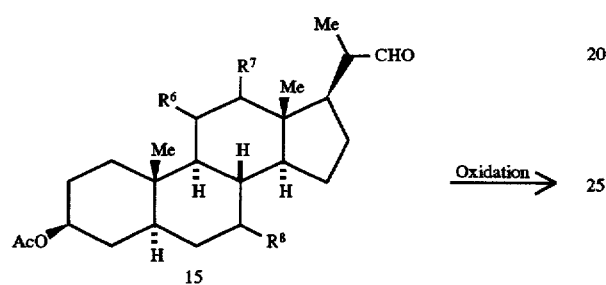
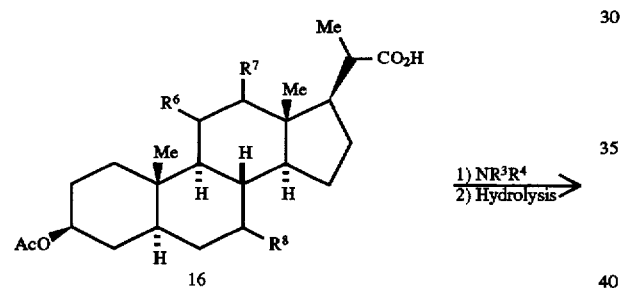
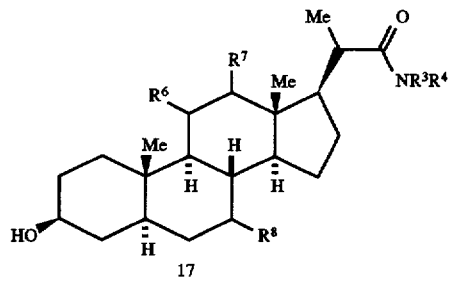
As shown in Scheme 4, aldehyde 15 can be selectively reduced using a mild reducing agent, for example, sodium borohydride, to give alcohol 18. Alcohol 18 can be converted to carbamate derivative 19 using various isocyanates, followed by acetate hydrolysis, to give compound 20.
SCHEME 4
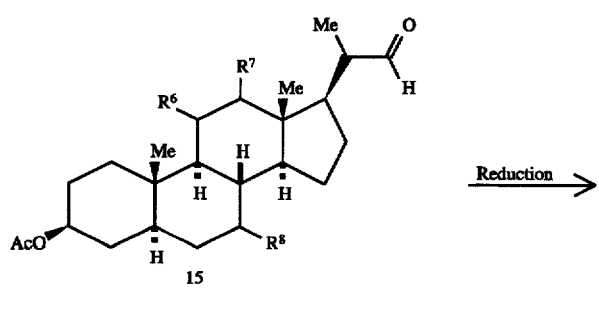
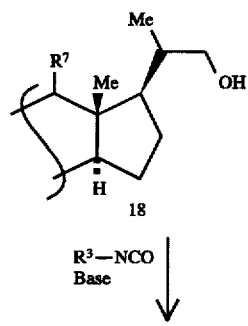

-continued
SCHEME 4

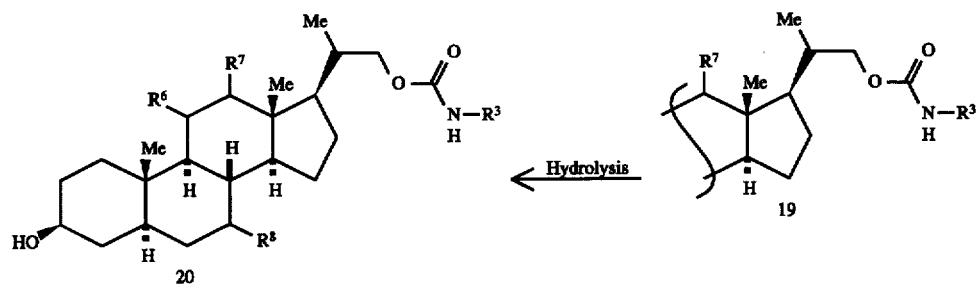

Synthesis of ether derivatives (Scheme 5) can be achieved using standard methods [*J. March in Advanced Organic Chemistry*, Chapter 10, 4th Ed., Wiley Interscience, 1992, pp 386–387, and references cited therein]. The standard methods involve treatment of a halide with an alkoxide prepared from alcohol 18, or mixing the halide and alcohol directly with base such as KOH in polar solvent such as DMSO, or with HgO and $HBF_4$ in $C_2Cl_2$. Hydrolysis of the acetate provides compound 22.

For the conversion of alcohol 18 to amino derivative 23, alcohol 18 can be convened to a reactive intermediate having a good leaving group such as halide, mesylate, or tosylate, using standard methods (Scheme 6). Treatment of these active intermediates with azide anion, followed by triphenyphosphine can afford amino derivative 23. Alternatively, a type of Mitsunobu reaction can be employed. For example, alcohol 18 can be treated with hydrazoic acid, diazodicarboxylate, and excess $Ph_3P$, followed by water or aqueous acid. Amine 23 can be treated with alkyl chloroformates or isocyanates using standard methods to provide various analogs 24. Treatment of amine 23 with an alkylating agent followed by an acylating agent can provide disubstituted amine analog 24. Hydrolysis of the acetate gives the free alcohol 25.

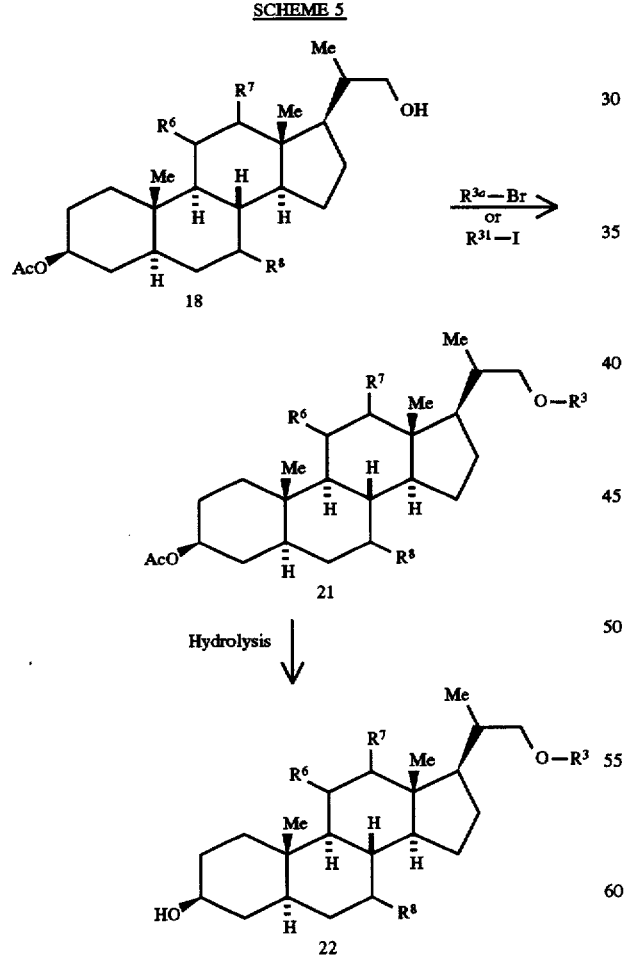

SCHEME 5

SCHEME 6

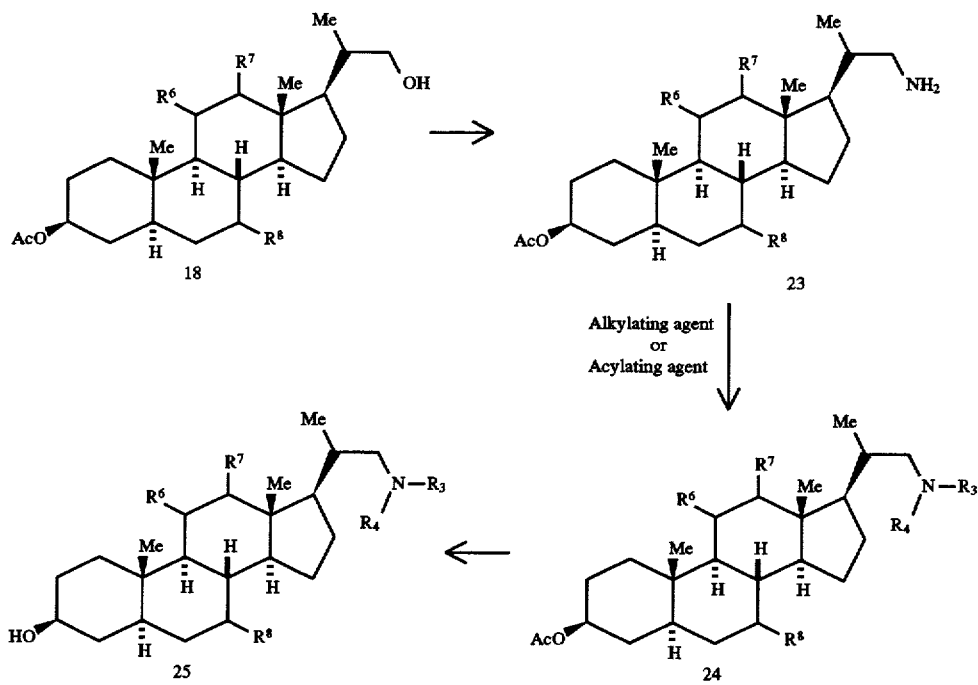

Various alkyl or aryl groups can be added to aldehyde 15 using standard methods such as aldol type reaction, Wittig reaction, or Homer-Emmons-Wittig reaction. Hydrolysis of an olefin derivative 26 can give compound 27 for coupling reaction with glycosyl-Q. Olefin derivative 26 can be hydrogenated to give compound 28.

Amino compound 29 can be prepared from aldehyde 15 by standard reductive amination methods employing, for example, $H_2$ and hydrogenation catalyst, Zinc and HCl, sodium triacetoxyborohydride, $BH_3$-pyridineNaBH$_4$, or NaBH$_3$CN [J. March in Advanced Organic Chemistry, Chapter 16, 4th Ed., Wiley Interscience, 1992, pp 898–900,

SCHEME 7

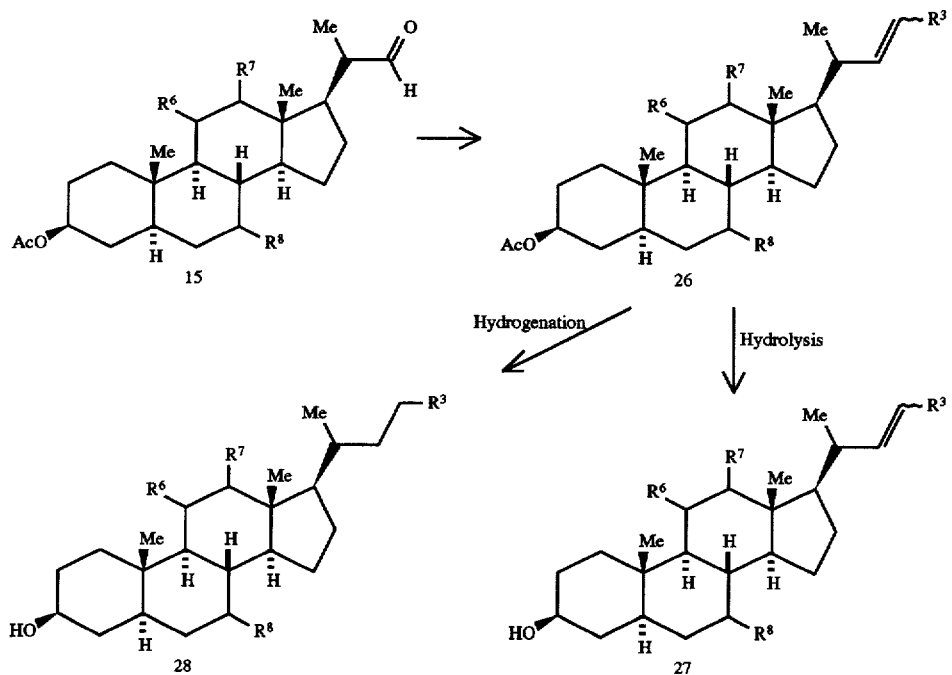

and references cited therein](Scheme 8). Acetate hydrolysis can afford free alcohol 30. Amino compound 29 can be further treated with appropriate reagents such as alkyl halide, acyl or aryl halide, alkyl or aryl chloroformate, alkyl or aryl isocyanate, and alkyl or aryl sulfonylisocyanate, followed by hydrolysis of the 3-OAc group, to give analogs of formula 31.

protecting group such as TBDMS if acetate can not be tolerated. In this case, the TBDMS protecting group can be removed with n-Bu$_4$NF. For example, a procedure similar to that described in *J. Org. Chem.*, (1980), 45, 3028, can be employed. Deprotection of 3-OR group in compound 33 followed by coupling with glycosyl-Q leads to the final product. Compound 33 can be further utilized after oxidative

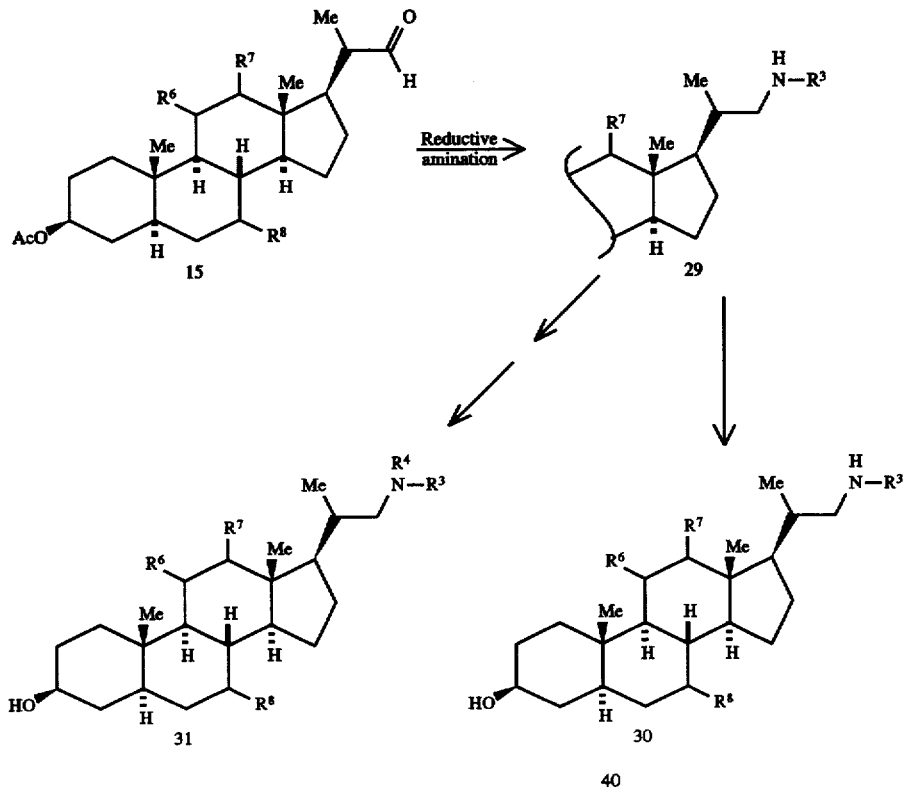

SCHEME 8

As shown in Scheme 9, 11-keto compound 32 can be converted to 12-keto analog 33 by standard 1,2-carbonyl transposition methods, wherein R is an appropriate robust cleavage to form using methods similar to those described in Schemes (2–8).

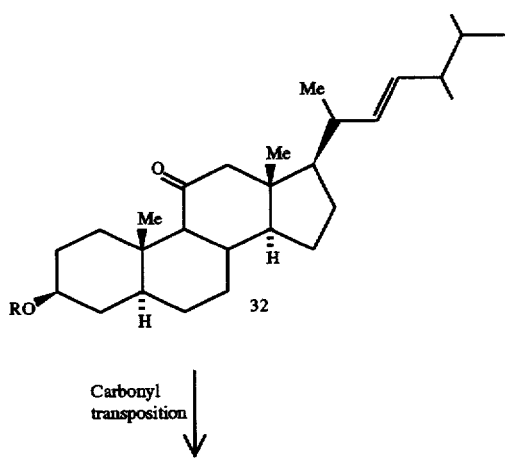

SCHEME 9

-continued
SCHEME 9

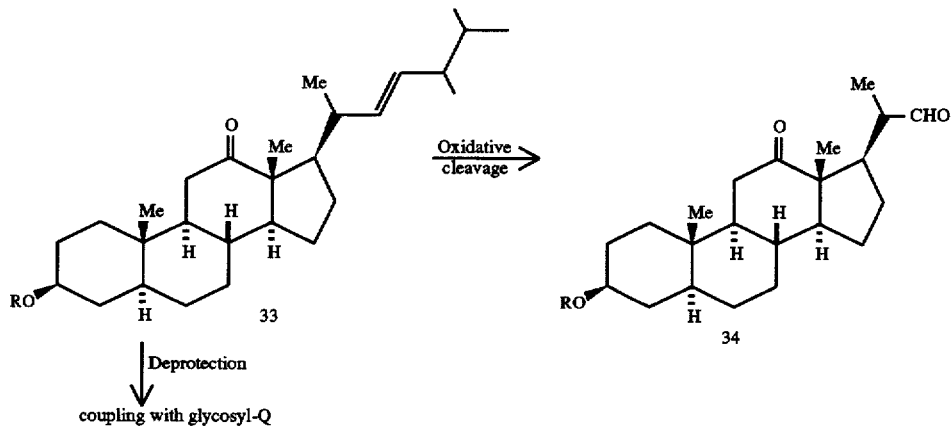

11- or 12-keto compound can be convened to the corresponding 11- or 12-sulfonyl compound 36 using a similar procedure as described in *Tetrahedron Lett.*, (1994), 35, 1691; *Chem. Lett.* (1973), 479, (Scheme 10). Sulfonyl compound 36 can be converted to reduced compound 37 by standard hydrogenation methods. Sulfonyl compound 36 can be treated with an appropriate reagent suitable for 1,4-addition such as alkyl lithium or aryl lithium to give the Michael adduct 38.

pound 39 according to a procedure similar to that described in *J. Chem. Soc. Perkin. Tran.* 1 (12), 3087–3089, (1991). Reduction of the carbonyl can afford compound 40. Compound 40 can be used for the synthesis of ether derivatives 41A or carbamate derivatives 41B as described in Schemes 4 and 5. Reductive amination of carbonyl compound 39 can give compound 42 as described in Scheme 8.

SCHEME 10

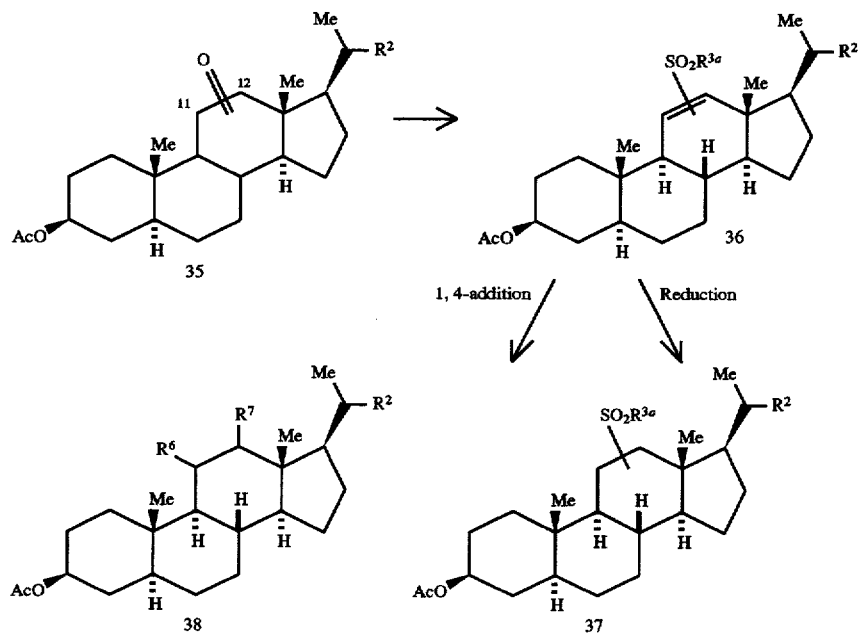

wherein one of $R^6$ or $R^7$ is $-SO_2R^{3a}$ and the other is $C_1-C_4$ alkyl or phenyl As shown in Scheme 11, aldehyde 35-i (wherein R is a robust protecting group) can be converted to carbonyl com-

SCHEME 11

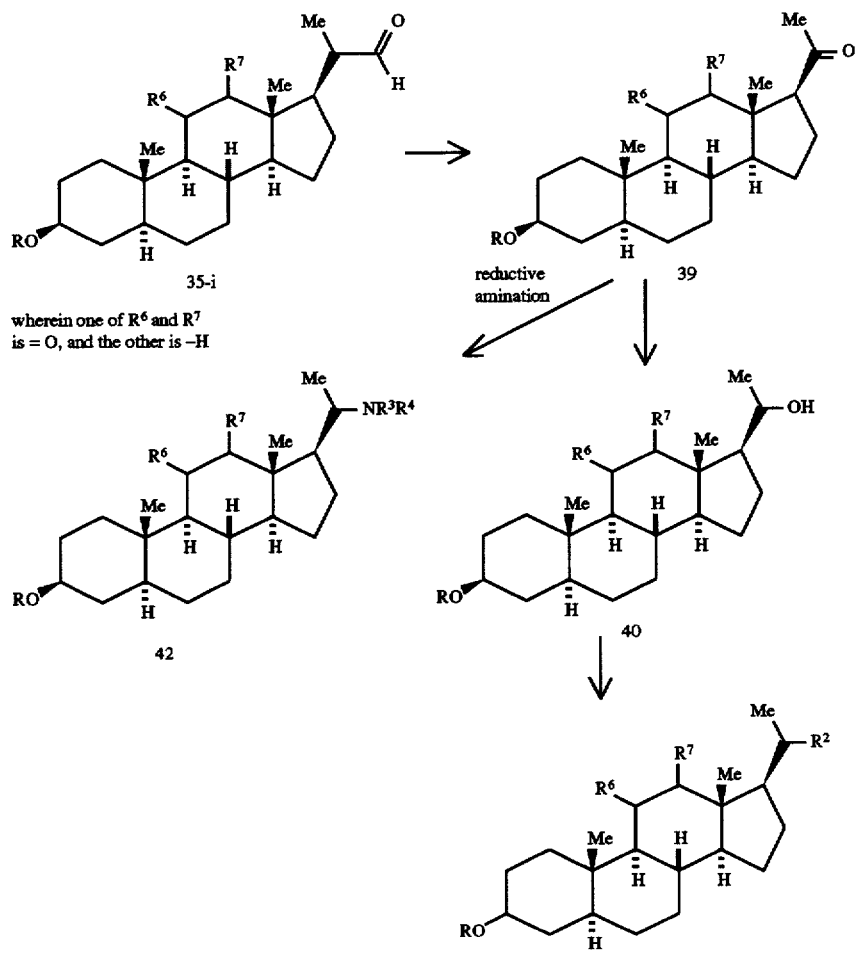

41A: $R^2 = -OR^3$
41B: $R^2 = -OCO-NH-R^3$

Alternatively, amino derivative 42 can be prepared by standard methods for amide synthesis such as Curtius rearrangement, from acid 16 (Scheme 12). Carboxylic acid 16 can be converted to acyl azide 44 using a variety of conditions. For example, the acid chloride prepared from carboxylic acid 16 by standard methods, can be reacted with sodium azide to provide acyl azide 44, which can be pyrolized to yield isocyanate 45. Isocyanate 45 can be treated with an appropriate alcohol or amine to give carbamate 46A and urea 46B, respectively.

SCHEME 12

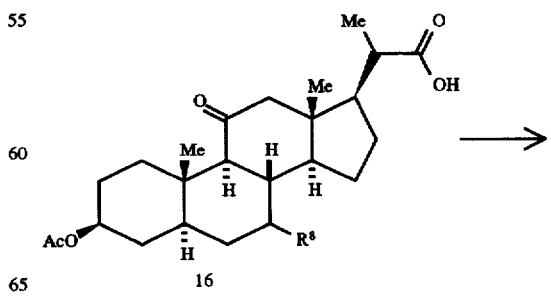

SCHEME 12

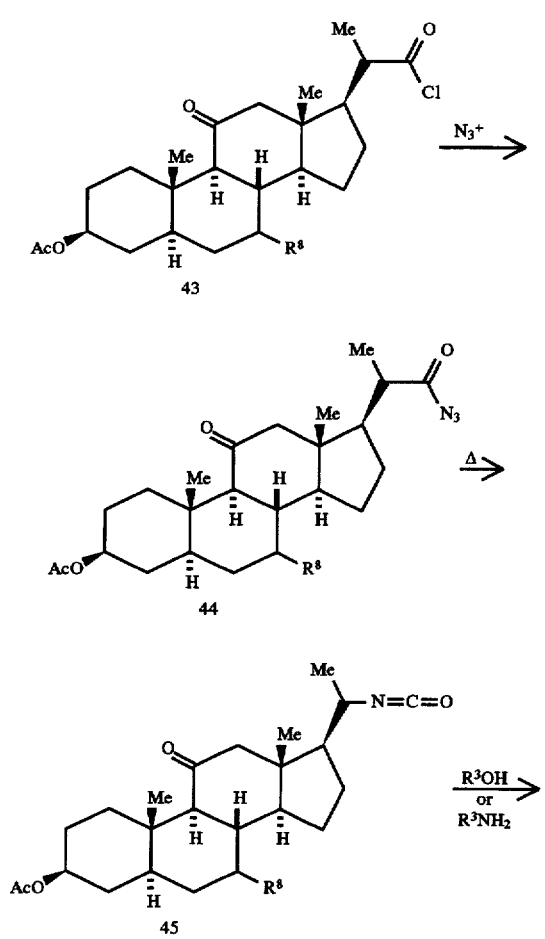

46A: $R^2 = -NHCOOR^3$
46B: $R^2 = -NHCONHR^3$

As depicted in Scheme 13, compounds of structural formula (I) can be prepared by alterative routes wherein X' is glycoside having protecting groups such as acetates, TBDMS, triethylsilyls, or chloroacetyls, or the like. The steroid can be coupled to glycosyl-Q first, and then the olefin (at the 22 position) in steroidal-glycoside 47 can be cleaved by standard oxidative cleavage methods such as ozonolysis to give aldehyde 48, which is convened to appropriate intermediates using procedures similar to those described in Schemes 2–12.

SCHEME 13

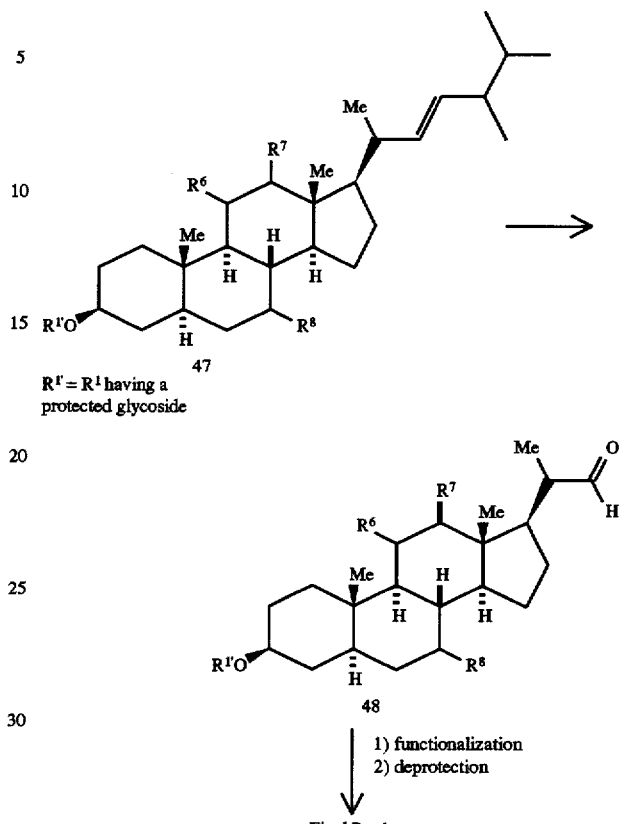

$R^{1'} = R^1$ having a protected glycoside

β-aryloxy glycosides can be incorporated into the steroid as shown in Scheme 14.

SCHEME 14

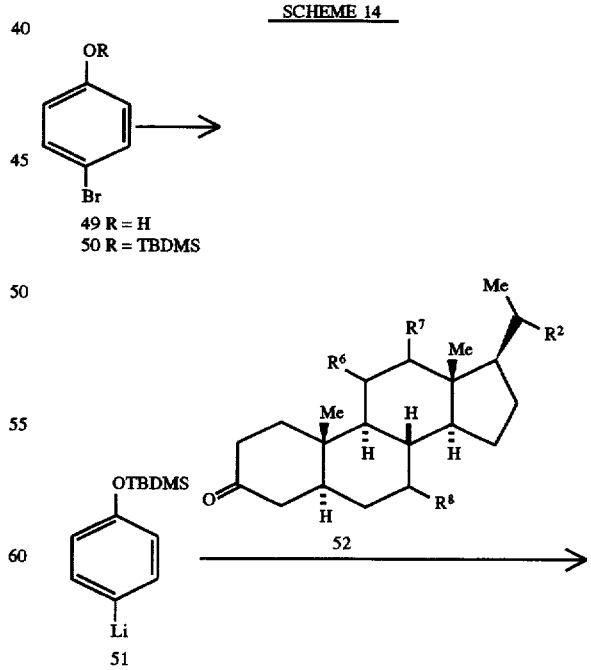

49 R = H
50 R = TBDMS

-continued
SCHEME 14

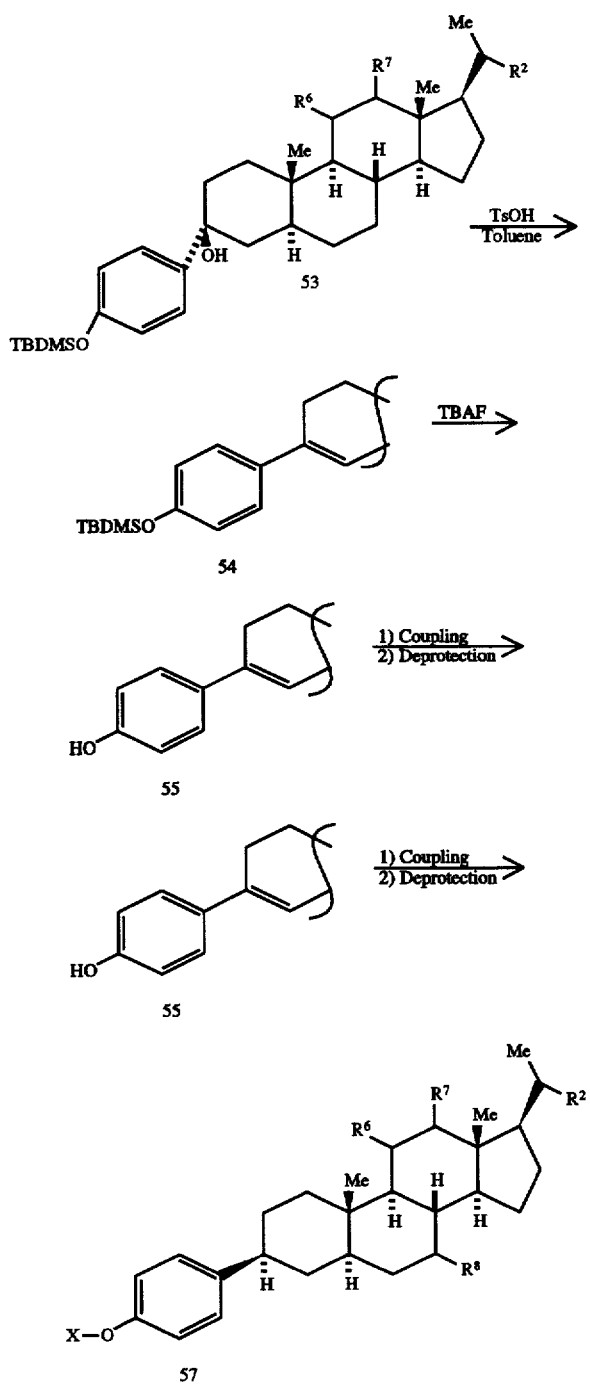

4-Halophenol, for example, 4-bromophenol 49 can be protected with a protecting group stable to alkyl or aryl metals such as the t-butyl dimethylsilyl ether group as in 50. Treatment of 50 with 2 equivalents of butyl lithium can generate the aryl lithium species 51 (*J. Org. Chem.*, 1988, 752–753 and *J. Org. Chem.*, 1989, 610–612). Addition to a solution of the ketone 52 (conveniently prepared from the corresponding alcohol by oxidation with, e.g., pyridinium chlorochromate; other functional groups may or may not have to be protected) can give the alcohol 53. Dehydration with a catalytic amount of acid such as p-toluenesulphonic acid can give the alkene 54. The silyl protecting group (or other if utilized) can be removed to give phenol 55. Glycosylation either as described before or by O-alkylation of the phenolate anion under phase transfer conditions can be followed by deprotection to give 56 (*Carbohydrate Res.* 1985, 333–337). The olefin can be reduced from the α-face by catalytic hydrogenation over a catalyst such as palladium on carbon to give the β-stereoisomer 57.

β-O-arylsteroidal glycosides can be prepared as outlined in Scheme 15. A protected sugar such as the glucose derivative 58 (other sugars can also be used) can be oxidized to the lactone 59 using a similar procedure to that described in *J. Org. Chem.* 2531, 1967. Addition of 51 to a solution of 59 followed by immediate reduction of the crude product can give the β-aryl sugar 60 (*J. Org Chem.* 610, 1989 and *J. Org. Chem.* 752, 1988). Deprotection of the silyl ether can give the phenol 61. The 3-α-hydroxy steroid 62 can be prepared by reduction of the ketone 52 (shown in scheme 14) with a reducing agent such as K-Selectride (*J. Chem Soc. Chem. Comm.* 1239, 1982). The aryl glycoside 61 can be attached to 62 via inversion of the 3-hydroxy group under the conditions of the Mitsunobu reaction using a similar procedure to that described in *Helv. Chim. Acta.* 60, 417, 1977, to give compound 63. Removal of the glycosyl protecting groups by hydrogenation gives compound 64. The use of other suitably protected sugar starting materials would provide other members of this class of β-O-aryl steroidal glycosides.

SCHEME 15

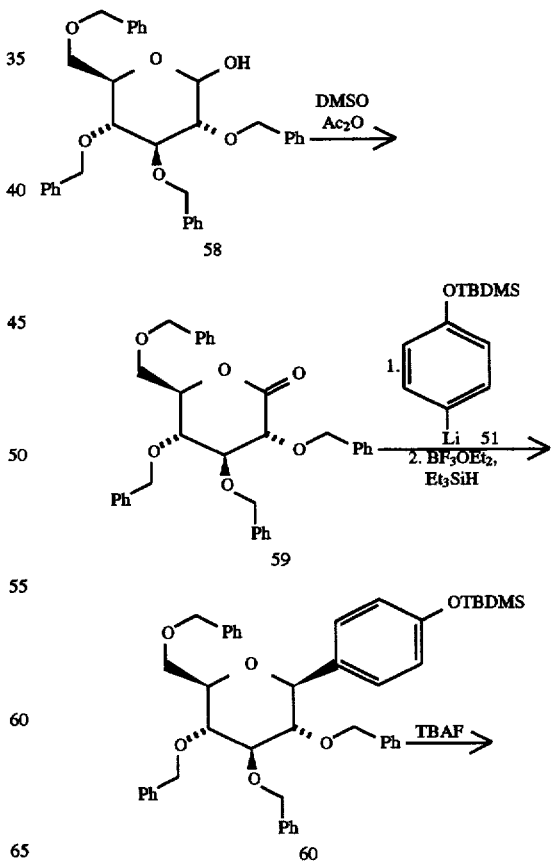

-continued
SCHEME 15

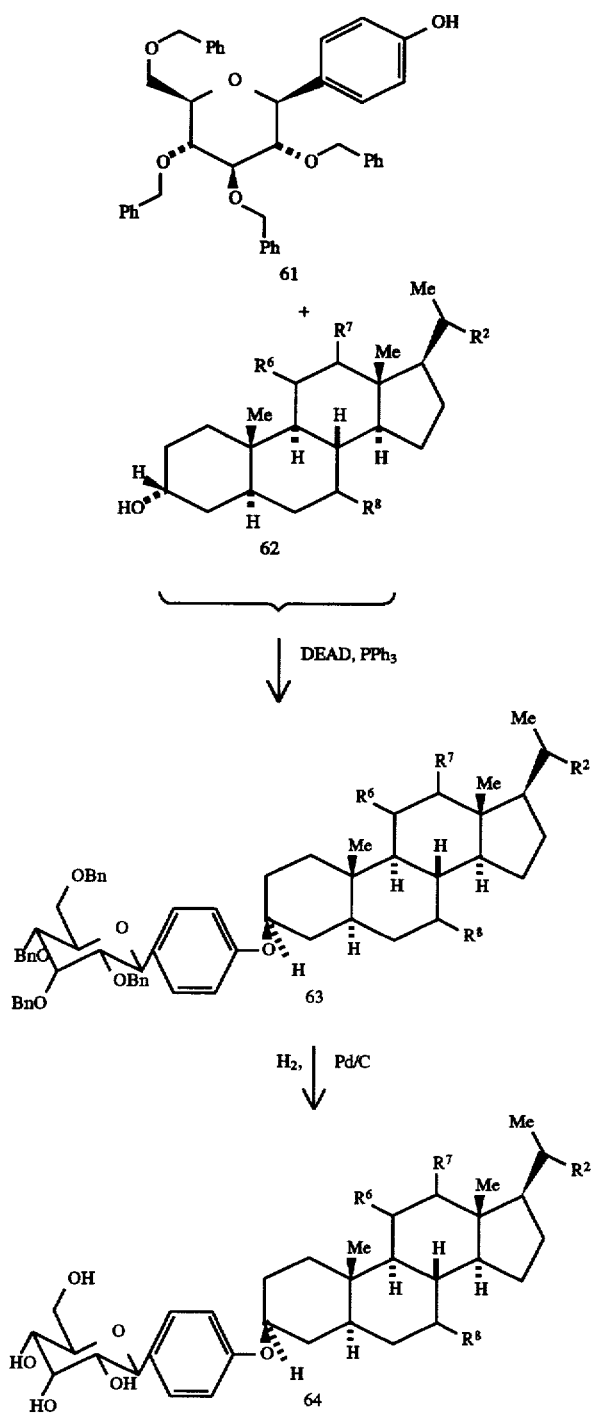

The compounds of this invention are potent inhibitors of cholesterol absorption and thus have therapeutic use as hypercholesterolemia controlling agents in mammals, particularly humans. Furthermore, the instant compounds are useful for the prevention and treatment of diseases associated with hypercholesterolemia, such as atherosclerosis, particularly arteriosclerosis. The compounds can be used to halt or slow the progression of atherosclerosis in mammals, particularly in hypercholesterolemic mammals. Atherosclerosis encompasses vascular diseases and conditions that are recognized and understood by physicians practicing in the relevant fields of medicine. Arteriosclerosis, atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the term "atherosclerosis."

Standard atherosclerosis risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. People who are identified as having one or more of the above-noted risk factors are intended to be included in the group of people considered at risk for developing atherosclerosis.

The hypercholesterolemia controlling activity of the instant compounds may be demonstrated by methods based on standard procedures. For example, the in vivo activity of these compounds in inhibiting intestinal absorption of cholesterol may be determined by the procedure of Melchoir and Harwell (*J. Lipid Res.*, 1985, 26, 306–315).

Activity can be determined by the amount of hypocholesterolemic agent that reduces cholesterol absorption, relative to the control, in male golden Syrian hamsters. Male golden Syrian hamsters are administered either a cholesterol-free diet (control animals) or a diet supplemented with 1% cholesterol and 0.5% cholic acid for 4 days. The following day, the animals are fasted for 18 hours, then administered a 1.5 mL oral bolus of water containing 0.25% methylcellulose, 0.6% Tween 80 and 10% ethanol (control animals) or an oral bolus that contains, in addition, the desired concentration of the compound to be tested. Immediately following bolus administration, the animals receive a second 1.5 mL oral bolus of liquid hamster diet containing 1% [$^3$H] cholesterol (2.0 mCi/animal; 210 dpm/nmol) and 0.5% cholic acid, and are fasted for an additional 24 hours. At the end of this second fasting period, animals are sacrificed, livers are excised, saponified, and aliquots are decolorized by addition of hydrogen peroxide, and assessed for radioactivity. Total hepatic radioactivity is calculated based on measured liver weight. The degree of cholesterol absorption is expressed as a percentage of the total radioactivity administered as an oral bolus that is present in the liver 24 hours following bolus administration.

Anti-atherosclerotic effects of the compounds can be determined by the amount of agent that reduces the lipid deposition in the rabbit aorta. Male New Zealand white rabbits are fed a diet containing 0.4% cholesterol and 5% peanut oil for 1 week (meal-fed once a day). After 1 week, the rabbits are dosed daily with the desired concentration of the compound to be tested. After 8.5 weeks, drug treatment is discontinued and the animals are maintained on the cholesterol containing diet for an additional 2 weeks and then switched to a cholesterol-free diet for 5 weeks. The animals are sacrificed, and the aortas removed from the thoracic arch to the branch of the iliacs. The aortas are cleaned of adventilia, opened longitudinally and then stained with Sudan IV as described by Holman et al., (*Lab. Invet.* 1958, 7, 42–47). The percent of the surface area stained is quantitated by densitometry using an Optimas Image Analyzing System (Image Processing Systems). Reduced lipid deposition is indicated by a reduction in the percent surface area stained in the drug treated group in comparison with the control rabbits.

Administration of the compounds of this invention can be via any method which delivers the compounds to the intestinal lumen. These methods include oral routes, intraduodenal routes, etc.

The compounds of the present invention can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. The compounds of the present invention may also be administered by other systemic routes such as, for example, by suppositors. An effective but non-toxic amount of the compound desired can be employed as a cholesterol-lowering agent.

The dosage regimen utilizing the compounds of the present invention is selected in accordance with a variety of factors including type, species, age, weight, sex and medical condition of the patient; the severity of the condition to be treated; the route of administration; the particular compound or salt thereof employed, and on the judgment of the prescribing physician. An ordinarily skilled physician or veterinarian can readily determine and prescribe the effective amount of the drug required to prevent, counter or arrest the progress of the condition. An effective dosage is in the range of 0.71 to 200 mg/kg/day, preferably 2 to 50 mg/kg/day, most preferably 2 to 7 mg/kg/day. For an average 70 kg human, this would amount to 0.05 to 14 g/day, preferably 0.14 to 3.5 g/day, most preferably 0.14 to 0.5 g/day.

Compounds of the present invention may be administered in a single daily dose, or the total daily dosage may be administered in divided doses of two, three or four times daily. The dosage can be administered at any time during the day, but is preferably administered with or before a meal. Therapy with the instant compounds may continue for as long as the patient is in need of cholesterol lowering treatment.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

Liquid pharmaceutically administerable composition can be prepared by dissolving or dispersing, or otherwise preparing the compound of the present invention and mixing it optionally with a pharmaceutical adjuvant in carrier, such as, for example, water, saline, aqueous dextrose, glycerol, ethanol and the like, to thereby form a solution suspension.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Methods of preparing pharmaceutical compositions are known in the an and can be found, for example, in Remington's Pharmaceutical Sciences, Mack Publishing Co., 15th Ed. (1975).

The compounds of this invention may also be administered in combination with other cholesterol lowering agents such as those which inhibit an enzymatic pathway in the biosynthesis of cholesterol. Examples of additional active agents which could be used in combination with the instant compounds include but are not limited to HMG-CoA reductase inhibitors; HMG-CoA synthase inhibitors; squalene epoxidase inhibitors; squalene synthetase inhibitors (also known as squalene synthase inhibitors), acylcoenzyme A: cholesterol acyltransferase (ACAT) inhibitors; probucol; niacin; fibrates such as clofibrate, fenofibrate, and gemfibrizol; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); aspirin; beta-blockers; and anti-oxidant vitamins such as vitamin C and E and beta carotene.

Illustrative of such HMG-CoA reductase inhibitors are lovastatin and related compounds as disclosed in U.S. Pat. No. 4,231,938; simvastatin and related compounds such as disclosed in U.S. Pat. Nos. 4,450,171; 4,346,227 pravastatin and related compounds such as disclosed in U.S. Pat. No. 4,346,227; fluvastatin and related compounds such as disclosed in WO 84/02131; and atorvastatin as disclosed in U.S. Pat. No. 5,273,995. Examples of HMG-CoA synthase inhibitors are: the beta-lactone derivatives disclosed in U.S. Pat. Nos. 4,806,564, 4,816,477, 4,847,271, and 4,751,237; the beta lactam derivatives disclosed in U.S. Pat. No. 4,983,597; and the substituted oxacyclopropane analogues disclosed in European Patent Publication EP O 411 703. The squalene synthetase inhibitors suitable for use herein include, but are not limited to, those disclosed by Biller et al., J. Med. Chem., 1988 Vol. 31, No. 10, pp. 1869–1871, including isoprenoid (phosphinylmethyl)-phosphonates such as those of the formula

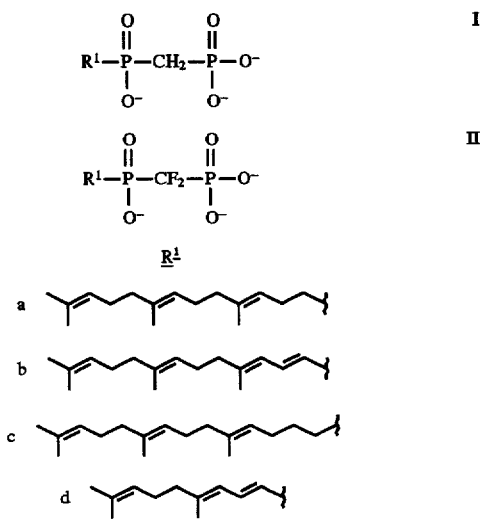

including the triacids thereof, triesters thereof and tripotassium and trisodium salts thereof as well as other squalene synthetase inhibitors disclosed in pending U.S. Pat. Nos. 4,871,721 and 4,924,024 and in Biller et al., *J. Med. Chem.*, 1988, Vol. 31, No. 10, pp. 1869 to 1871.

In addition, other squalene synthetase inhibitors suitable for use herein include the terpenoid pyrophosphates disclosed by P. Ortiz de Montellano et al., *J. Med. Chem.*, 1977, 20, 243–249, the farnesyl diphosphate analog A and presqualene pyrophosphate (PSQ-PP) analogs as disclosed by Corey and Volante, *J. Am. Chem. Soc.* 1976, 98, 1291–1293, phosphinylphosphonate reported by McClard, R. W. et al., *J.A.C.S.*, 1987, 109, 5544 and cyclopropanes reported by Capson, T. L., PhD dissertation, June, 1987, *Dept. Med. Chem. U. of Utah*, Abstract, Table of Contents, pp. 16, 17, 40–43, 48–51, Summary.

Further, the benzodiazipine squalene synthase inhibitors described in EP O 567 026 to Takeda Chemical Industries, the quinuclidinyl squalene synthase inhibitors described in PCT publications WO 94/03451, WO 93/09115, WO 93/21183, WO 93/21184, WO 93/24486, and U.S. Pat. No. 5,135,935, may be employed in combination with the 5a-reductase inhibitors of the present invention. In addition, the zaragozic acid type squalene synthase inhibitors as described in U.S. Pat. Nos. 5,284,758; 5,283,256; 5,262,435; 5,260,332; 5,264,593; 5,260,215; 5,258,401; 5,254,727; 5,256,689; 5,132,320; 5,278,067, and PCT Publications WO 92/12156; WO 92/12157; WO 92/12158; WO 92/12159; WO 92/12160; WO 93/18040; WO 93/18039; WO 93/07151; and European Patent Publications EP O 512 865, EP O 568 946; EP O 524,677 and EP O 450 812, as well as the acyclic tricarboxylic acid compounds U.S. Pat. No. 5,254,727, may be employed. Illustrative examples of squalene epoxidase inhibitors are disclosed in European Patent Publication EP O 318 860 and in Japanese Patent Publication JO2 169-571A. LDL-receptor gene inducer molecules are disclosed in U.S. patent application Ser. No. 07/670,640 filed Mar. 18, 1991. Other cholesterol lowering agents that may be administered include niacin, probucol, and the fibric acids, clofibrate and gemfibrozil.

The dose of HMG-CoA reductase inhibitor contemplated for use in the co-administration of the present invention are from about 1 to 200 mg per day, preferably given in single or divided doses. Most preferred are dosages from 5 to 80 mg per day.

The doses of HMG-CoA synthase inhibitor contemplated for use in the co-administration of the present invention are from about 20 to 200 mg, preferably given in single or divided doses.

The doses of squalene synthase inhibitor contemplated for use in the co-administration of the present invention are from about 2 to 2000 mg per day, preferably given in single or divided doses.

The doses of squalene epoxidase inhibitor contemplated for use in the co-administration of the present invention are from 2 to 200 mg per day, preferably given in single or divided doses.

Representative of additional combinations are those containing 0.05 g to 14 g of a cholesterol absorption inhibitor of structural Formula (I) in combination with up to 1000 mg probucol, up to 2 g clofibrate, 0.5 to 8 g of niacin, 800 to 1500 mg gemfibrozil or fenofibrate, or 20 to 300 mg of an LDL receptor gene inducer.

The cholesterol absorption inhibitors of the present invention may also be co-administered with pharmaceutically acceptable nontoxic cationic polymers capable of binding beta acids in a non-resorbable form in the gastrointestinal tract. Examples of such polymers include cholestyramine, colestipol, and poly[methyl-(3-trimethylaminopropyl) imino-trimethylene dihalide].

The relative amounts of the compounds of this invention and these polymers is between 1:100 and 1:15,000.

For combination treatment with more than one active agent, where the active agents are in separate dosage formulations, the active agents can be administered concurrently, or they each can be administered at separately staggered times.

In the following examples, certain compounds are defined by the following formula II structure:

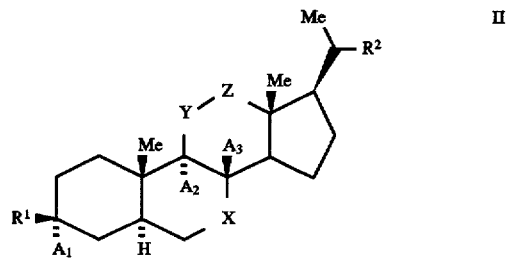

The compounds defined by formula II in the examples below are within the generic scope of formula I. Other compounds referred to in the examples are defined by the structures shown in the schemes, and are noted as such.

EXAMPLE 1

(3β,5α)-3-[(β-D-cellobiosyl)oxy]-ergost-22-en-11-one. Formula II, wherein $R^1$=D-(cellobiosyl)oxy-, $R^2$=3',4'-dimethyl-1'-pentenyl, $A_1$=$A_2$=$A_3$=H, X=Z=$C_2$, Y=C=O

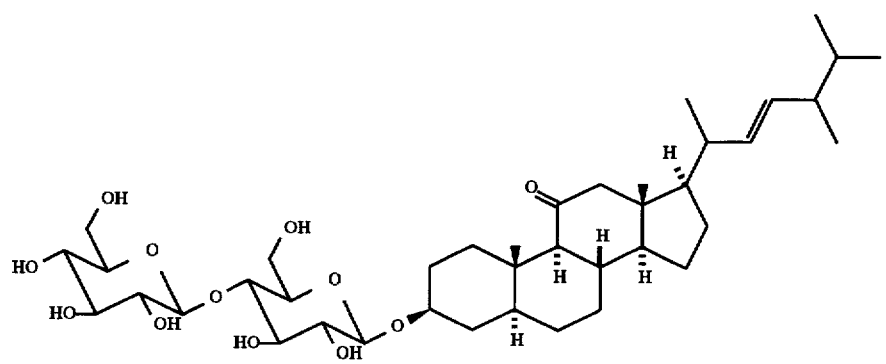

Step 1: Preparation of (3β,5α)-3-[(Heptaacetyl-β-D-cellobiosyl)oxy]-ergost-22-en11-one To a suspension of (3β,5α)ergost-22-en-3-ol-11-one(1 g, 2.41 mmol) and anhydrous zinc fluoride (1 g, 9.67 mmol) was added heptaacetylβ-D-cellobiosyl bromide (3 g, 4.29 mmol) at room temperature. The reaction mixture was stirred at 70 °C. for 3 h, and at rt overnight. After the addition of 0.5 mL of water the reaction mixture was diluted with $CH_2Cl_2$ (50 mL), and was stirred at rt for 2 h. After filtration of insoluble material filtrate was concentrated. Flash chromatography (H:E=6:1, 1:1) afforded the titled compound.

MS: 1055 (M+Na)

EXAMPLE 3

Formula II, wherein $R^1$=D-(cellobiosyl)oxy-, $R^2$=3',4'-dimethyl-1-pentanyl, $A_1$=$A_2$=$A_3$=H, X=Z=$C_2$, Y=CO

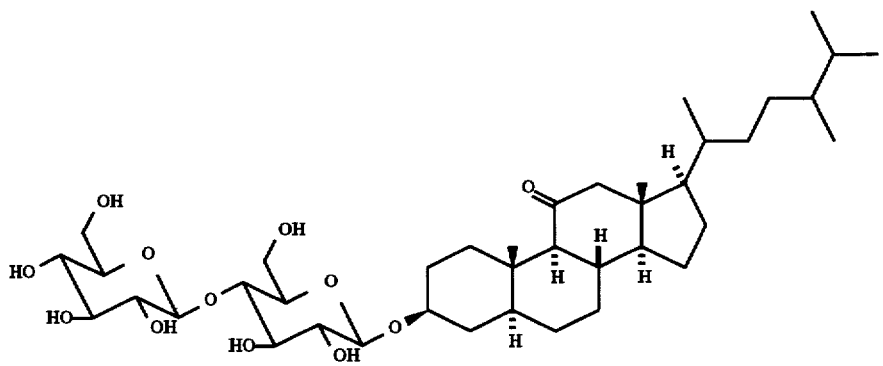

Step 2: Preparation of (3β,5α)-3-[(β-D-cellobiosyl)oxy]-ergost-22-en-11-one

A mixture of (3β,5α)-3-[(Heptaacetyl-β-D-cellobiosyl) oxy]-ergost-22-en-11one (400 mg), sodium methoxide solution in MeOH (25%, 1 mL), methanol (2 mL) and THF (3 mL) was heated to reflux for 4 h, and was stirred at rt for 2 h. AcOH (2 mL) was added to destroy the excess sodium methoxide. After evaporation of solvents toluene was added and evaporated to remove AcOH. The residual white solid was dissolved in $CHCl_3$/MeOH (4:1), and flash chromatographed ($C_2Cl_2$/MeOH=10:1, $CHCl_3$/MeOH=4:1) to give the titled compound.

MS: 761 (M+Na)

EXAMPLE 2

Formula II, wherein $R^1$=D-(cellobiosyl)oxy-, $R^2$=3',4'-dimethyl-1'-pentenyl, $A_1$=$A_2$=$A_3$=H, X=Z=$C_2$, Y=C=N—OH Step 1: Preparation of compound 2 in Scheme 1, wherein, —OX'=D-(Heptaacetyl-β-D-cellobiosyl)oxy-, $R^2$=3',4'-dimethyl-1'-pentanyl, $R^7$=$R^8$=H, $R^6$=oxo To a solution of (3β,5α)-3-[(Heptaacetyl-β-D-cellobiosyl)-oxy]-ergost-22-en-11-one. (320 mg) in MeOH (10 mL) was added 10% Pd/C. The reaction mixture equipped with $H_2$ balloon was stirred at rt overnight. After filtration through Celite filtrate was concentrated to give the titled compound.

MS: 1056 (M+Na)

Step 2: Preparation of Formula II, wherein, $R^1$=-(β-D-cellobiosyl)oxy-, $R^2$=3',4'-dimethyl-1'-pentanyl, $A_1$=$A_2$=$A_3$=H, X=Z=$CH_2$, Y=CO

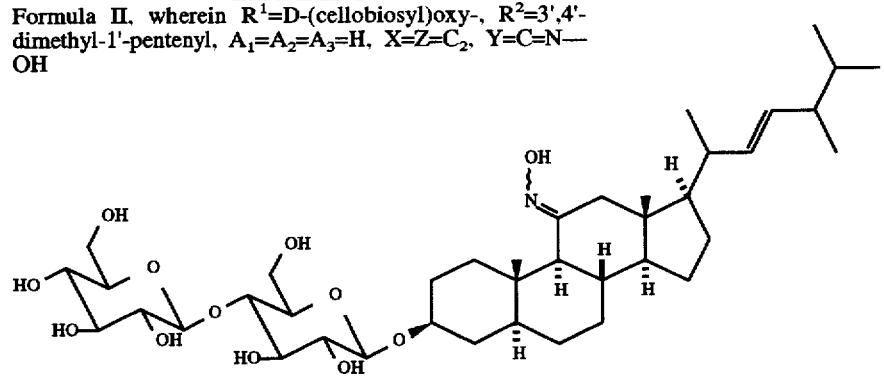

A mixture of (3β,5α)-3-[(β-D-cellobiosyl)oxy]-ergost-22-en-11-one (100 mg, 0.135 mmol), $NH_2OH.HCl$ (94 mg, 1.35 mmol), $Et_3N$ (41 mL), and pyridine (5 mL) was refluxed for 72 h. After concentration the residue was purified by flash chromatography ($C_2Cl_2$/MeOH=10:1, $CHCl_3$/MeOH=4:1) to give the titled compound.

MS: 754 (M+H)

A mixture of (3β,5α)-3-[(Heptaacetyl-β-D-cellobiosyl) oxy]-ergostan-11-one (240 mg), sodium methoxide solution in MeOH (25%, 0.2 mL), MeOH (2 mL) and THF (4 mL) was heated to reflux for 3 h. AcOH (1 mL) was added to destroy the excess sodium methoxide. After evaporation of solvents toluene was added and evaporated to remove AcOH. The residual white solid was dissolved in $CHCl_3$/MeOH (4:1), and flash chromatographed ($CH_2Cl_2$/MeOH=10:1, $CHCl_3$/MeOH=4:1) to give the titled compound.

MS: 763 (M+Na)

EXAMPLE 4

Formula II, wherein R¹=-β-D-(cellobiosyl)oxy-, R²=—CON-dibenzyl, A₁=A₂=A₃=H, X=Z=CH₂, Y=C=O

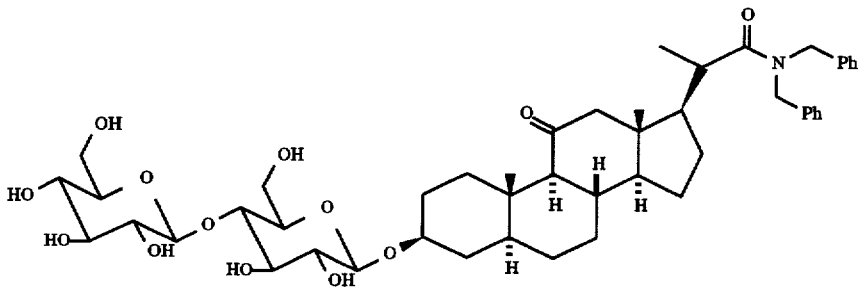

Step 1: Preparation of compound 15 in Scheme 3, wherein, R⁷=R⁸=H, R⁶=oxo

Ozone was passed through a solution of 3β-acetoxy-5a-ergost-22-en-11-one 14 (3 g, 6.58 mmol) in a mixture of CH₂Cl₂ (100 mL) and MeOH (10 mL) at −78° C. for 20 min. To the above solution was added dimethyl sulfide (10 mL) in one portion at −78° C. After the removal of the dry ice/acetone bath the reaction was stirred at rt overnight. Concentration in vacuo was followed by flash chromatography to give the titled compound as a white solid.

MS: 389 (M+H)

NMR (300 MHz, CDCl₃), d 9.50 (d, 1H, J=2.0 Hz), 4.52–4.66 (m, 1H), 2.37–2.48 (m, 2H), 2.20–2.30 (m, 2H), 0.75–1.78 (m, 19H), 1.03 (d, 3H, J=6.9 Hz), 0.97 (s, 3H), 0.60 (s, 3H).

Step 2: Preparation of compound 16 in Scheme 3, wherein, R⁷=R⁸=H, R⁶=oxo

A solution of the aldehyde from step 1 (1.05 g, 2.71 mmol) in t-BuOH (17 mL) was diluted with an aqueous 5% NaH₂PO₄ (11 mL) at 0° C. With vigorous stirring 1M-KMnO₄ (16 mL) was added to the above solution. After being stirred at rt for 1 h the reaction was quenched with saturated aqueous Na₂SO₃. pH was adjusted to 3 with 2 N—HCl. After the extraction with CHCl₃ (3×) the solution was washed with brine and was dried over anhydrous MgSO₄. Concentration gave the titled compound as a white solid.

Step 3: Preparation of

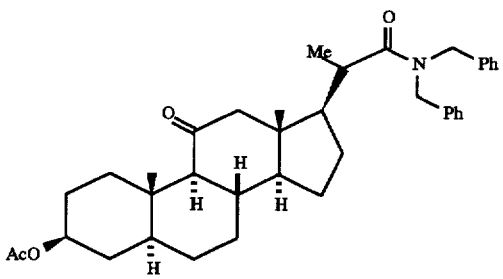

To a solution of the product from step 2 (1.08 g, 2.67 mmol), HOBT (433 mg, 3.20 mmol) and EDC (768 mg, 4.01 mmol) in CH₂Cl₂ (10 mL) was added dibenzylamine (631 mg, 3.20 mmol) at rt. The reaction was stirred at rt for 18 h. After concentration the residue was partitioned between EtOAc and 2N—HCl. Organic layer was washed with saturated aqueous NaHCO₃ and brine, and was dried over anhydrous MgSO₄. Concentration gave the titled compound as a white solid.

¹H NMR (400 MHz, CDCl₃) d 7.06–7.35 (m, 10H), 4.33–4.66 (m, 5H), 1.96 (s, 3H), 1.05 (d, 3H, J=6.7 Hz), 0.97 (s, 3H), 0.45 (s, 3H).

MS:

Step 4: Preparation of

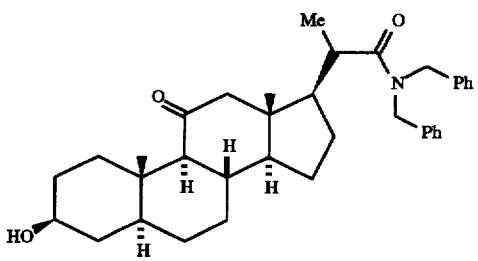

To a solution of the product of step 3 (610 mg, 1.04 mmol) in THF (4 mL) and MeOH (2 mL) was added 25% NaOMe solution in MeOH (0.1 mL) at rt. The reaction was refluxed for 1 h. After concentration the residue was partitioned between CHCl₃ and 2N—HCl. Aqueous layer was extracted with CHCl₃ (2×). Organic layer was washed with brine and was dried over anhydrous MgSO₄. Concentration gave the title compound as a white solid.

¹H NMR (400 MHz, CDCl₃) d 7.12–7.36 (m, 10H), 4.38–4.67 (m, 4H), 3.55 (m, 1H), 2.64 (m, 1H), 2.33–2.47 (m, 3H), 1.95–2.14 (m, 2H), 0.77–1.78 (m, 18H), 1.08 (d, 3H, J=6.7 Hz), 0.97 (s, 3H), 0.48 (s, 3H).

MS: 542 (M+H).

Step 5: Preparation of Formula II, wherein R¹=-(Heptaacetyl-β-D-cellobiosyl)oxy-, R²=—CON-dibenzyl, A₁=A₂=A₃=H, X=Z=CH₂, Y=C=O The titled compound was prepared according to the method described in Example 1, Step 2.

MS: 1160 (M+H)

Step 6: Preparation of Formula II, wherein R¹=-(β-D-cellobiosyl)oxy-, R²=—CON-dibenzyl, A₁=A₂=A₃=H, X=Z=CH₂, Y=C=O The title compound was prepared according to the method described in Example 1, Step 3.

MS: 866 (M+H)

EXAMPLE 5

Formula II, wherein R¹=-β-D-(cellobiosyl)oxy-, R²=—CONH-3'4'5'-trimethoxy-phenyl, A₁=A₂=A₃=H, X=Z=CH₂, Y=C=O

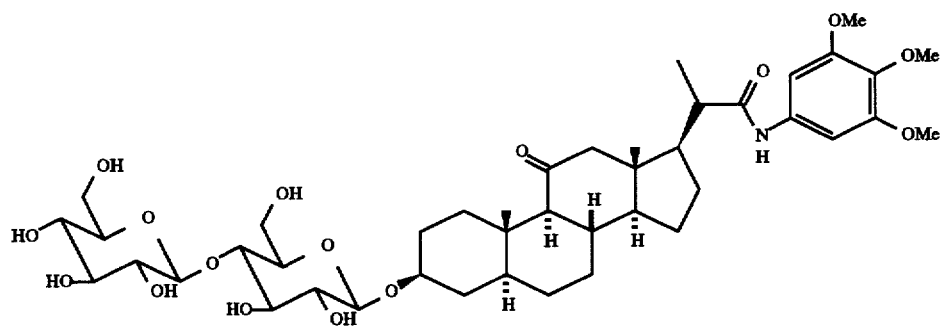

The titled compound was prepared by using a similar procedure to that described in Example 4.

MS: 852 (M+H)

EXAMPLE 6

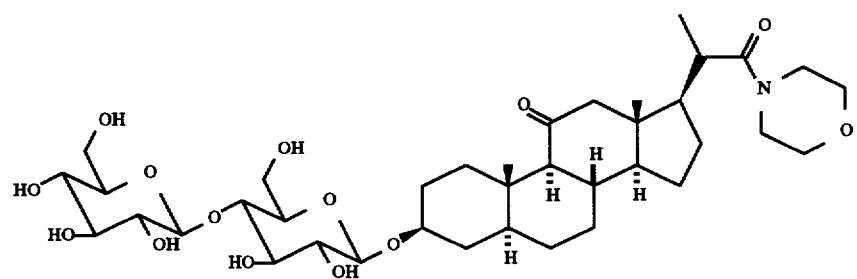

The above compound was prepared by using a similar procedure to that described in Example 4.

MS: 756 (M+H)

EXAMPLE 7

Formula II, wherein $R^1 = \beta$-D-(cellobiosyl)oxy-, $A_1 = A_2 = A_3 = H$, $X = Z = CH_2$, $Y = C = O$, $R^2 = $—CO—NH-4'-propylphenyl

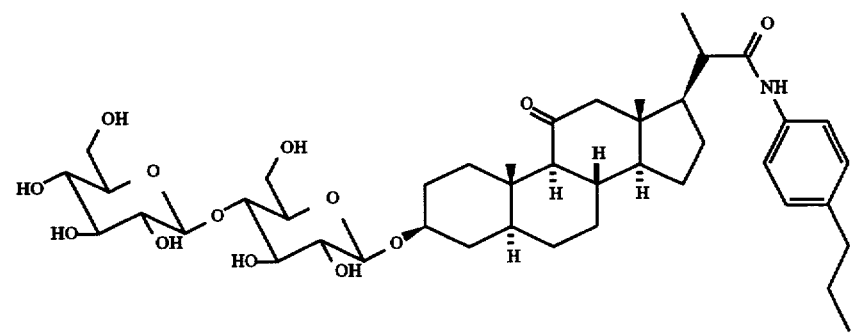

The titled compound was prepared by using a similar procedure to that described in Example 4.

MS: 804 (M+H)

EXAMPLE 8

Formula II, wherein $R^1 = \beta$-D-(cellobiosyl)oxy-, $A_1 = A_2 = A_3 = H$, $X = Z = CH_2$, $Y = C = O$, $R^2 = $—CO—N-dipentyl

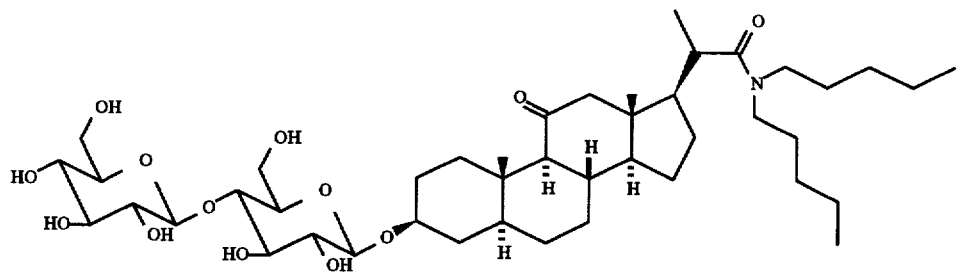

Step 1: Preparation of compound 48 in Scheme 13, wherein $R^7=R^8=H$, $R^6$ is oxo, $R^1=[(Heptaacetyl-\beta-D-cellobiosyl)oxy]$-

Ozone was passed through a solution of 5 g of the compound

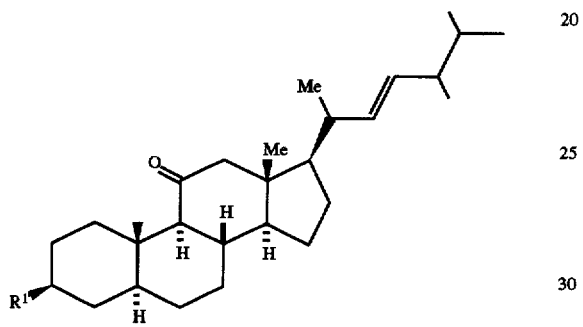

wherein $R^1= [(heptaacetyl-\beta-D-cellobiosyl)oxy]$ in $CH_2Cl_2$ (100 mL) at −78° C. for 15 min. To the above solution was added dimethyl sulfide (10 mL) in one portion at −78° C. After the removal of the dry ice/acetone bath the reaction was stirred at rt overnight. Concentration in vacuo was followed by flash chromatography (H:E=1:1) to give the titled compound as a white solid.

MS: 965 (M+H)

Step 2: Preparation of Formula II, wherein $R^1$=Heptaacetyl-β-D-(cellobiosyl)oxy-, $A_1=A_2=A_3=H$, $X=Z=CH_2$, $Y=CO$, $R^2$=—$CO_2H$ The titled compound was prepared according to the method described in Example 4, Step 2.

MS: 981 (M+H)

Step 3: Preparation of Formula II, wherein $R^1$=Heptaacetyl-β-D-(cellobiosyl)oxy-, $A_1=A_2=A_3=H$, $X=Z=CH_2$, $Y=C=O$, $R^2$=—CO—N-dipentyl The titled compound was prepared according to the method described in Example 5, Step 1.

Step 4: Preparation of Formula II, wherein $R^1$=β-D-(cellobiosyl)oxy-, $A_1=A_2=A_3=H$, $X=Z=CH_2$, $Y=C=O$, $R^2$=—CO—N-dipentyl The title compound was prepared according to the method described in Example 1, Step 2.

MS: 826 (M+H)

EXAMPLE 9

Formula II, wherein $R^1$=-β-D-(cellobiosyl)oxy-, $A_1=A_2=A_3=H$, $X=Z=CH_2$, $Y=C=O$, $R^2$=—$C_2OH$:

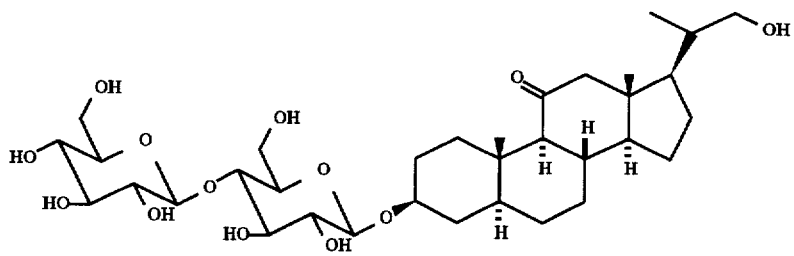

Step 1: Preparation of Formula II, wherein $R^1$=Heptaacetyl-β-D-(cellobiosyl)oxy-, $A_1=A_2=A_3$=H, X=Z=$CH_2$, Y=C=O, $R^2$=—$CH_2OH$ To a solution of aldehyde (883 mg, 0.92 mmol) in EtOH (5 mL) was added $NaBH_4$ (42 mg, 1.1 mmol) (the aldehyde is the compound of Formula II wherein wherein $R^1$=heptaacetyl-β-D-(cellobiosyl)oxy-, $A_1=A_2=A_3$=H, X=Z=$CH_2$, Y=C=O, and $R^2$=—CHO). The reaction was stirred at rt for 1 h. Evaporation of EtOH was followed by flash chromatography (H:E=1:1, 100% EtOAc) to give the title compound as a white solid.

MS: 984 (M+$NH_4$)

Step 2: Preparation of Formula II, wherein $R^1$=β-D-(cellobiosyl)oxy-, $A_1=A_2=A_3$=H, X=Z=$CH_2$, Y=C=O, $R^2$=—$CH_2OH$ The title compound was prepared according to the method described in Step 2 for the synthesis of Example 1.

MS: 695 (M+$NH_4$)

EXAMPLE 10

Formula II, wherein $R^1$=β-D-(cellobiosyl)oxy-, $A_1=A_2=A_3$=H, X=Z=$CH_2$, Y=C=O, $R^2$=—$CH_2$—CONH—Ph:

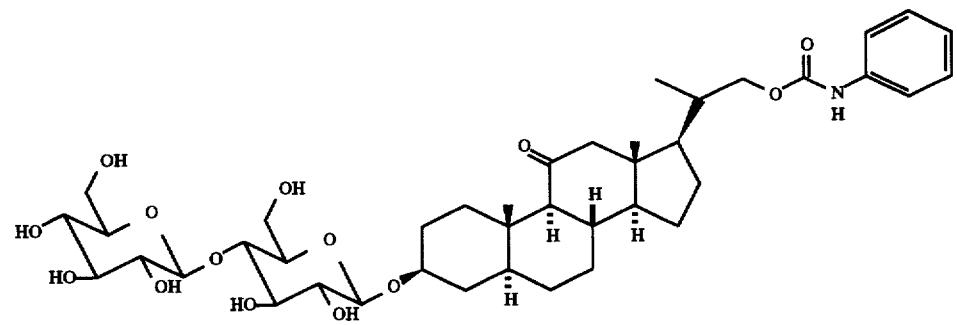

Step 1: Preparation of Formula II, wherein $R^1$=Heptaacetyl-β-D-(cellobiosyl)oxy-, $A_1=A_2=A_3$=H, X=Z=$CH_2$, Y=C=O, $R^2$=—CH2O—CONH—Ph To a solution of (3β,5α)-3-[(Heptaacetyl-β-D-cellobiosyl)oxy]-ergostan-11-on-22-hydroxy (120 mg, 0.12 mmol) in THF (5 mL) were added phenylisocyanate (0.1 mL, 0.92 mmol) and DBU. The reaction was refluxed for 3 h. The crude mixture was directly loaded onto the silica gel column. Flash chromatography (H:E=1:1) afforded the title compound as a white solid which is less polar than the starting alcohol.

MS: 1086 (M+H)

Step 2: Preparation of Formula II, wherein $R^1$=β-D-(cellobiosyl)oxy-, $A_1=A_2=A_3$=H, X=Z=$CH_2$, Y=C=O, $R^2$=—$CH_2O$—CONH—Ph The titled compound was prepared according to the method described in Step 2 for the synthesis of Example 1.

MS: 792 (M+H)

EXAMPLE 11

Formula II, wherein $R^1$=β-D-(cellobiosyl)oxy-, $A_1=A_2=A_3$=H, X=Z=$CH_2$, Y=C=O, $R^2$=—CO—NH—Ph:

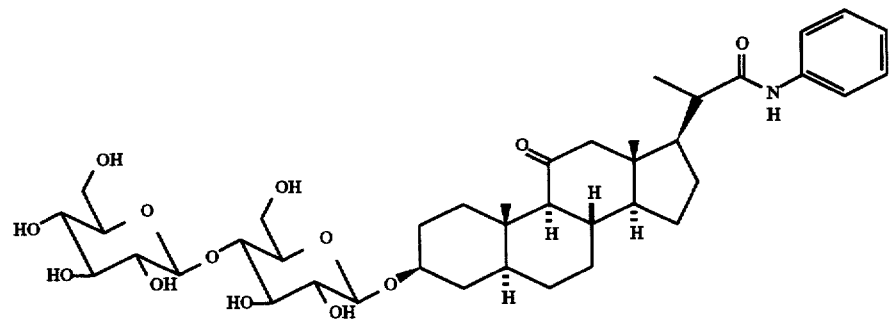

The titled compound was prepared by using a similar procedure to that described in Example 4.

MS: 762 (M+H)

EXAMPLE 12
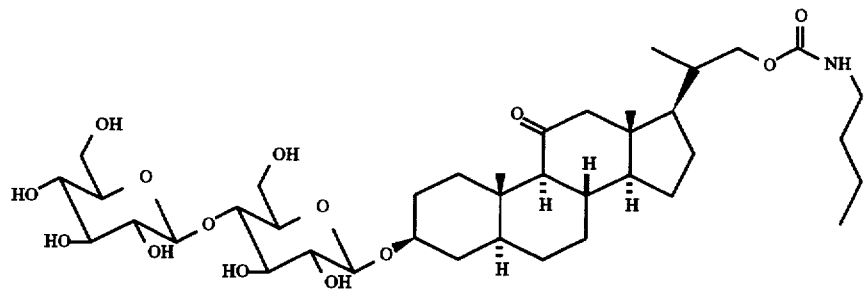
The above compound was prepared by using a similar procedure to that described in Example 10.
MS: 794 (M+Na)
EXAMPLE 13
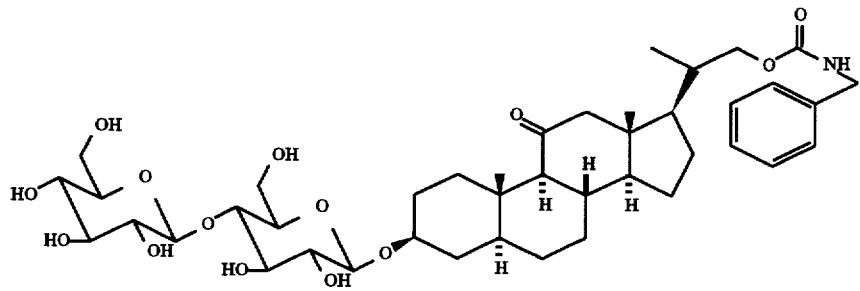
The above compound was prepared by using a similar procedure to that described in Example 10.
MS: 828 (M+Na)
EXAMPLE 14
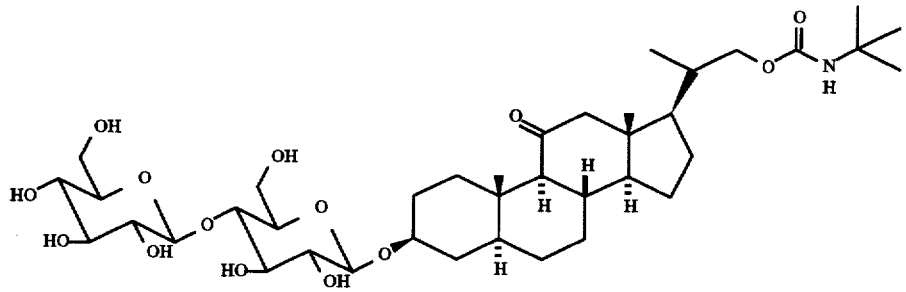
The above compound was prepared by using a similar procedure to that described in Example 10.

EXAMPLE 15
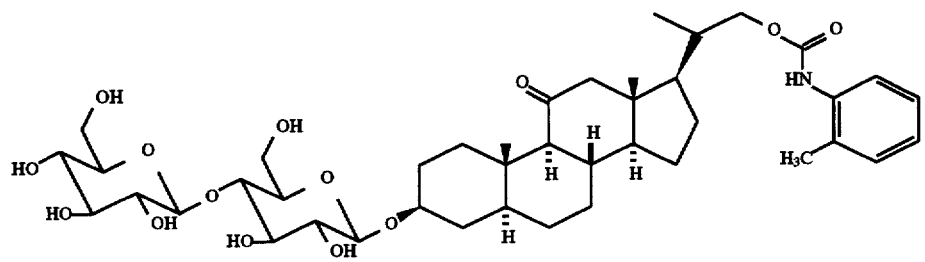
The above compound was prepared by using a similar procedure to that described in Example 10.
MS: 823 (M+NH$_4$)
EXAMPLE 16
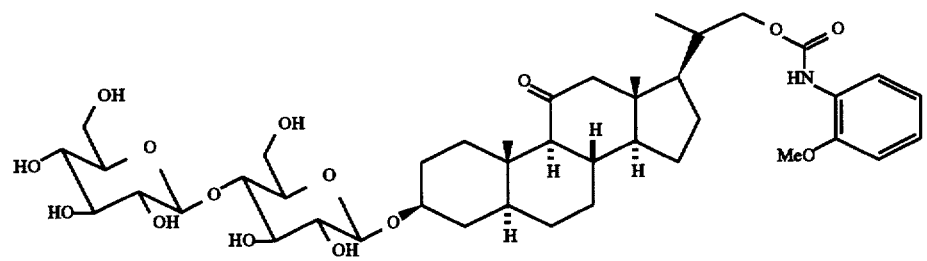
The above compound was prepared by using a similar procedure to that described in Example 10.
MS: 844 (M+Na)
EXAMPLE 17
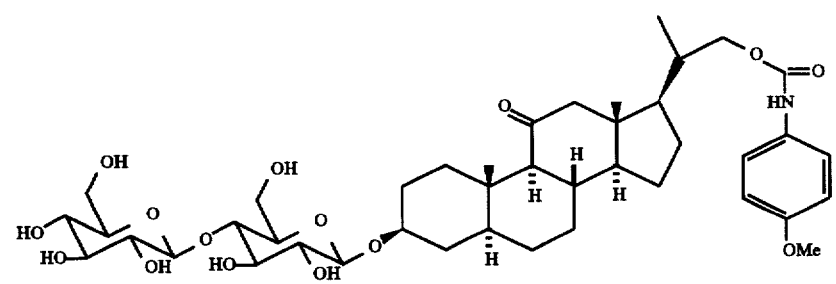
The above compound was prepared by using a similar procedure to that described in Example 10.
MS: 844 (M+Na)
EXAMPLE 18
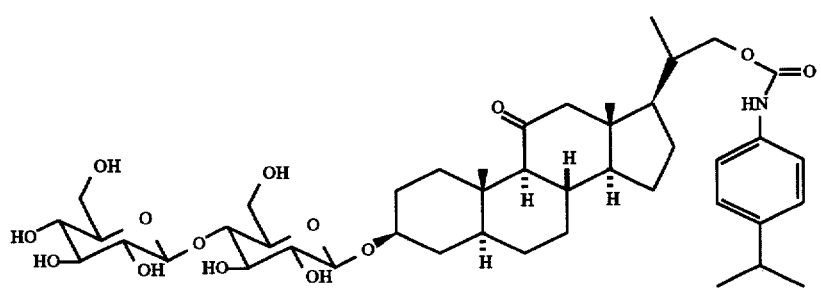

The above compound was prepared by using a similar procedure to that described in Example 10.
MS: 856 (M+Na)

MS: 891 (M+Na)

EXAMPLE 19

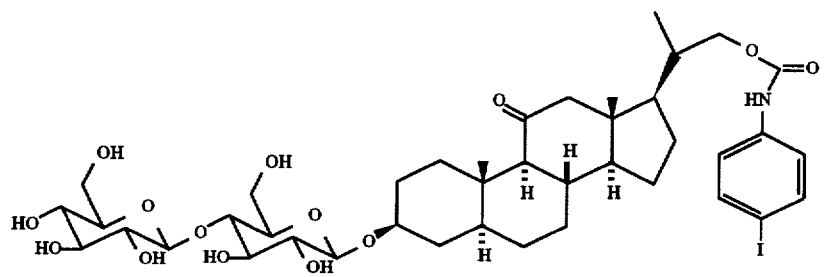

The above compound was prepared by using a similar procedure to that described in Example 10.
MS: 940 (M+Na)

EXAMPLE 20

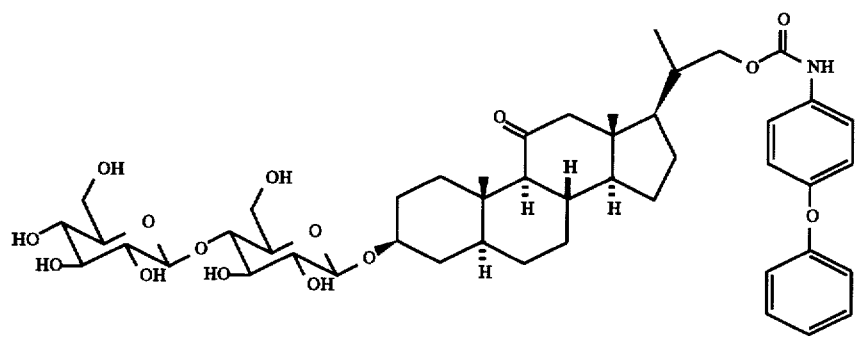

The above compound was prepared by using a similar procedure to that described in Example 10.
MS: 907 (M+Na)

EXAMPLE 21

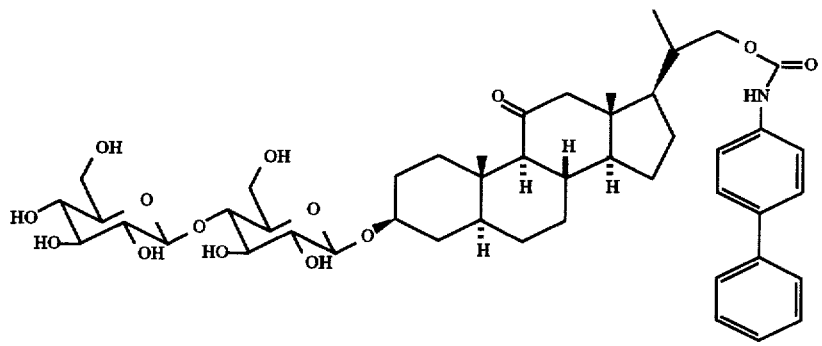

The above compound was prepared by using a similar procedure to that described in Example 10.

EXAMPLE 22

Preparation of

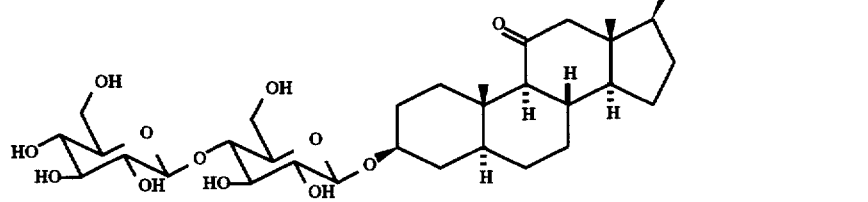

To a solution of benzyl diethyl phosphite in THF (1.5 mL) was added LDA (2M in heptane/THF/ethylbenzene, 0.187 mL) at −78° C. The solution was stirred at −78° C. for 15 min. To the above solution was added aldehyde (300 mg, 0.311 mmol) at −78° C. (the aldehyde is the compound of Formula II wherein $R^1$=D-(cellobiosyl)oxy; $R^2$=—CHO; $A_1$=$A_2$=$A_3$=—H, X=Z=—H; and Y=—C=O). After being stirred at −78° C. for 10 min., the temperature was allowed to increase to room temperature over 18 h. To the above orange colored solution was added NaOMe solution in MeOH (25%, 1 mL) and the solution was refluxed for 1 h. AcOH (1 mL) was added to destroy the excess sodium methoxide. After evaporation of solvents, toluene was added and evaporated to remove AcOH. The residual solid was dissolved in $CHCl_3$/MeOH (4:1), and flash chromatographed ($CH_2Cl_2$/MeOH=10:1, $CHCl_3$/MeOH=4:1) to give the title compound.

MS: 745 (M+1)

EXAMPLE 23

Preparation of

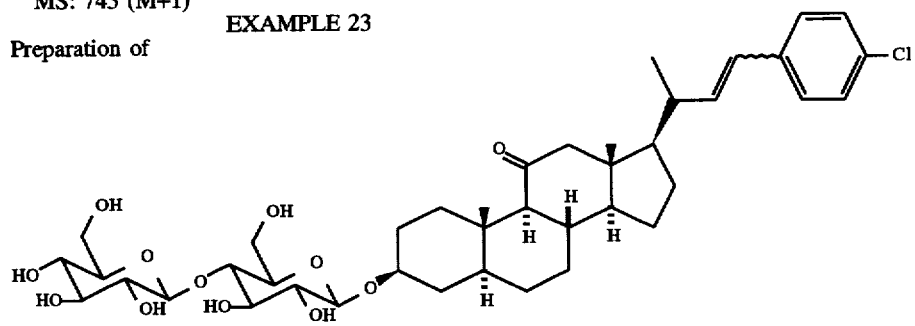

The above compound was prepared by using a similar procedure to that described in Example 22.

MS: 802 (M+Na)

EXAMPLE 24

Preparation of

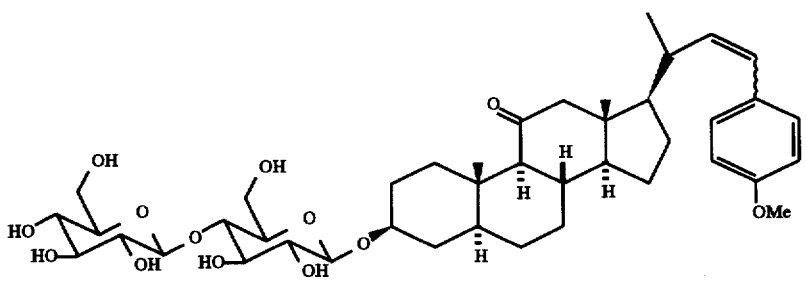

The above compound was prepared by using a similar procedure to that described in Example 22.

MS: 775 (M+1)

EXAMPLE 25

Preparation of

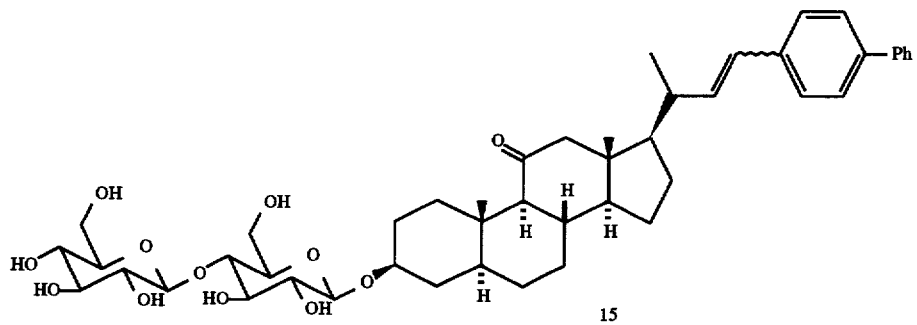

The above compound was prepared by using a similar procedure to that described in Example 22.

MS: 821 (M+1)

EXAMPLE 26

Preparation of

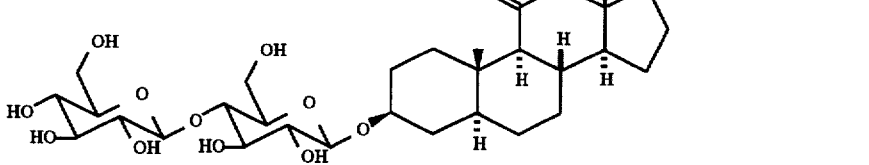

The above compound was prepared by using a similar procedure to that described in Example 22.

MS: 786 (M+NH$_4^+$)

EXAMPLE 27

Preparation of

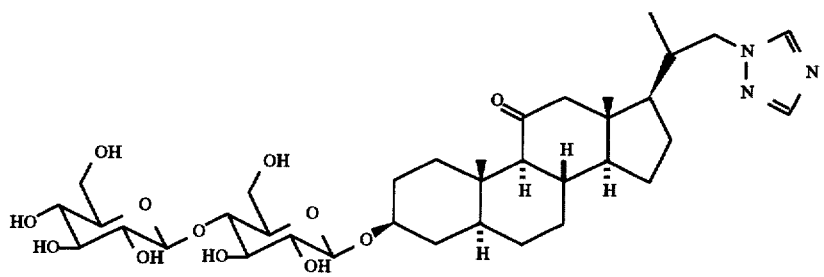

Step 1: Preparation of Formula II, wherein R$^1$=-Heptaacetyl-β—D-(cellobiosyl)oxy-, A$_1$=A$_2$=A$_3$=H, X=Z=CH$_2$, Y=C=O, R$^2$=—CH$_2$Br To a solution of the alcohol prepared in Step 1 for Example 9 (500 mg, 0.517 mmol) and triphenylphosphine (163 mg, 0.62 mmol) in CH$_2$Cl$_2$ (5 mL) was added carbon tetrabromide (206 mg, 0.62 mmol) at 0° C. The solution was stirred at 0° C. for 1 h and at rt for 1 h. The crude mixture was directly flash chromatographed (H:E=1:1) to give the title compound as a white solid.

Step 2: Preparation of Formula II, wherein R$^1$=-β—D-(cellobiosyl)oxy-, A$_1$=A$_2$=A$_3$=H, X=Z=CH$_2$, Y=C=O, R$^2$=—CH$_2$-1,2,4-triazole Hydrolysis was performed according to the method described in Step 2 for the synthesis of Example 1, to give the title compound.

MS: 724 (M+1)

Preferred compounds of this invention are those of formula Ia as defined below in Table I.

TABLE I

Ia

| | R⁸ | R⁶ | R⁷ | R¹ | R² |
|---|---|---|---|---|---|
| 1 | H | =O | —H | O-β-D-cellobiosyl | 3,4-dimethyl-1-pentenyl |
| 2 | H | =N—OH | —H | O-β-D-cellobiosyl | 3,4-dimethyl-1-pentenyl |
| 3 | H | —SO₂—CH₃ | —H | O-β-D-cellobiosyl | 3,4-dimethyl-1-pentenyl |
| 4 | H | —SO₂—Ph | —H | O-β-D-cellobiosyl | 3,4-dimethyl-1-pentenyl |
| 5 | H | —H | =O | O-β-D-cellobiosyl | 3,4-dimethyl-1-pentenyl |
| 6 | H | —H | =N—OH | O-β-D-cellobiosyl | 3,4-dimethyl-1-pentenyl |
| 7 | H | —H | —SO₂—CH₃ | O-β-D-cellobiosyl | 3,4-dimethyl-1-pentenyl |
| 8 | H | —H | —SO₂—Ph | O-β-D-cellobiosyl | 3,4-dimethyl-1-pentenyl |
| 9 | H | =O | —H | O-β-D-cellobiosyl | 3,4-dimethyl-pentanyl |
| 10 | H | =N—OH | —H | O-β-D-cellobiosyl | 3,4-dimethyl-pentanyl |
| 11 | H | —SO₂—CH₃ | —H | O-β-D-cellobiosyl | 3,4-dimethyl-pentanyl |
| 12 | H | —SO₂—Ph | —H | O-β-D-cellobiosyl | 3,4-dimethyl-pentanyl |
| 13 | H | —H | =O | O-β-D-cellobiosyl | 3,4-dimethyl-pentanyl |
| 14 | H | —H | =N—OH | O-β-D-cellobiosyl | 3,4-dimethyl-pentanyl |
| 15 | H | —H | —SO₂—CH₃ | O-β-D-cellobiosyl | 3,4-dimethyl-pentanyl |
| 16 | H | —H | —SO₂—Ph | O-β-D-cellobiosyl | 3,4-dimethyl-pentanyl |
| 17 | =O | =O | H | O-β-D-cellobiosyl | 3,4-dimethyl-1-pentenyl |
| 18 | =O | =O | H | O-β-D-cellobiosyl | 3,4-dimethyl-pentanyl |
| 19 | H | =O | H | O-β-D-cellobiosyl | —CH₂—OH |
| 20 | H | =O | H | O-β-D-cellobiosyl | —CH₂—O—CONH—Ph |
| 21 | H | =O | H | O-β-D-cellobiosyl | —CH₂—O—CONH-(4-iodo-Ph) |
| 22 | H | =O | H | O-β-D-cellobiosyl | —CH₂—O—CONH-(4-phenyl-Ph) |
| 23 | H | =O | H | O-β-D-cellobiosyl | —CH₂—O—CONH-(4-phenoxy-Ph) |
| 24 | H | =O | H | O-β-D-cellobiosyl | —CH₂—O—CONH-(4-iso-propyl-Ph) |
| 25 | H | =O | H | O-β-D-cellobiosyl | —CH₂—O—CONH-(2-methyl-Ph) |
| 26 | H | =O | H | O-β-D-cellobiosyl | —CH₂—O—CONH-(2-methoxy-Ph) |
| 27 | H | =O | H | O-β-D-cellobiosyl | —CH₂—O—CONH-(4-methoxy-Ph) |
| 28 | H | =O | H | O-β-D-cellobiosyl | —CH₂—O—CONH-(2-fluoro-Ph) |
| 29 | H | =O | H | O-β-D-cellobiosyl | —CH₂—O—CONH-(4-fluoro-Ph) |
| 30 | H | =O | H | O-β-D-cellobiosyl | —CH₂—O—CONH-(2-chloro-Ph) |
| 31 | H | =O | H | O-β-D-cellobiosyl | —CH₂—O—CONH-(4-chloro-Ph) |
| 32 | H | =O | H | O-β-D-cellobiosyl | —CH₂—O—CONH-tert-Bu |
| 33 | H | =O | H | O-β-D-cellobiosyl | —CH₂—O—CONH—Bn |
| 34 | H | =O | H | O-β-D-cellobiosyl | —CH₂—O—CONH-n-Bu |
| 35 | H | =O | H | O-β-D-cellobiosyl | —CH₂—O-tert-Bu |
| 36 | H | =O | H | O-β-D-cellobiosyl | —CH₂—O—Bn |
| 37 | H | =O | H | O-β-D-cellobiosyl | —CH₂—O-(4-nitro-Ph) |
| 38 | H | =O | H | O-β-D-cellobiosyl | —CH₂—O-(4-amino-Ph) |
| 39 | H | =O | H | O-β-D-cellobiosyl | —CH₂—O-(4-methane-sulfonyl-Ph) |
| 40 | H | =O | H | O-β-D-cellobiosyl | —CO—NH-(3,4,5-trimethoxy-Ph) |
| 41 | H | =O | H | O-β-D-cellobiosyl | —CO—NH-(4-propyl-Ph) |
| 42 | H | =O | H | O-β-D-cellobiosyl | —CO-morpholinyl |
| 43 | H | =O | H | O-β-D-cellobiosyl | —CO—N-(pentyl)₂ |
| 44 | H | =O | H | O-β-D-cellobiosyl | —CO—NH—Ph |
| 45 | H | =O | H | O-β-D-cellobiosyl | —CO—N—(Bn)₂ |
| 46 | H | =O | H | O-β-D-cellobiosyl | —CO—NH-(3,4-methylene-dioxy-Ph) |
| 47 | H | =O | H | O-β-D-cellobiosyl | —CO—NH-(2-methoxy-Ph) |
| 48 | H | =O | H | O-β-D-cellobiosyl | —CH=CH—Ph(trans) |
| 49 | H | =O | H | O-β-D-cellobiosyl | —CH=CH-(4-iso-propyl-Ph) |
| 50 | H | =O | H | O-β-D-cellobiosyl | —CH=CH-(4-phenyl-Ph) |
| 51 | H | =O | H | O-β-D-cellobiosyl | —CH=CH-(4-tert-butyl-Ph) |
| 52 | H | =O | H | O-β-D-cellobiosyl | —CH=C—(Ph)₂ |
| 53 | H | =O | H | O-β-D-cellobiosyl | —CH=CH-(3,4,5-trimethoxy-Ph) |
| 54 | H | =O | H | O-β-D-cellobiosyl | —CH=CH-(4-methoxy-Ph) |
| 55 | H | =O | H | O-β-D-cellobiosyl | —CH=CH-tert-Bu |
| 56 | H | =O | H | O-β-D-cellobiosyl | —CH₂NH—CO—NH—Ph |
| 57 | H | =O | H | O-β-D-cellobiosyl | —CH₂NH—CO—NH—Bn |
| 58 | H | =O | H | O-β-D-cellobiosyl | —CH₂NH—CO—NH—Bu |
| 59 | H | =O | H | O-β-D-cellobiosyl | —O—CO—NH—Ph |
| 60 | H | =O | H | O-β-D-cellobiosyl | —O—CO—NH—Bn |
| 61 | H | =O | H | O-β-D-cellobiosyl | —O—CO—NH—Bu |
| 62 | H | =O | H | O-β-D-cellobiosyl | —NH—CO—NH—Ph |
| 63 | H | =O | H | O-β-D-cellobiosyl | —NH—CO—NH—Bn |
| 64 | H | =O | H | O-β-D-cellobiosyl | —NH—CO—NH—Bu |

TABLE I-continued

Ia

|  | R⁸ | R⁶ | R⁷ | R¹ | R² |
|---|---|---|---|---|---|
| 65 | H | =O | H | O-β-D-cellobiosyl | —CH$_2$—SO$_2$—Ph |
| 66 | H | =O | H | O-β-D-cellobiosyl | —CH$_2$—SO$_2$—Bn |
| 67 | H | =O | H | O-β-D-cellobiosyl | —CH$_2$—SO$_2$—Bu |
| 68 | H | =O | H | O-β-D-cellobiosyl | —NH—SO$_2$—Ph |
| 69 | H | =O | H | O-β-D-cellobiosyl | —NH—SO$_2$—Bn |
| 70 | H | =O | H | O-β-D-cellobiosyl | —NH—SO$_2$—Bu |
| 71 | H | =O | H | O-β-D-cellobiosyl | —SO$_2$—Ph |
| 72 | H | =O | H | O-β-D-cellobiosyl | —SO$_2$—Bn |
| 73 | H | =O | H | O-β-D-cellobiosyl | —SO$_2$—Bu |

What is claimed is:

1. A compound of structural formula (I):

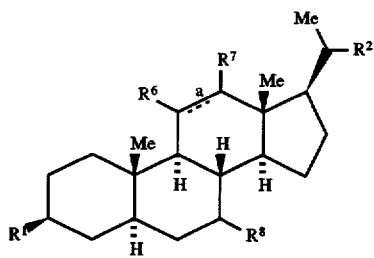

and the pharmaceutically acceptable salts and hydrates thereof wherein:

R¹ is selected from:
- a) —O—X,
- b) —O—phenyl substituted at the 3 or 4 position with X,
- c) -phenyl-4-O—X or β-phenyl-3-O—X, and wherein X is a sugar selected from β-D-cellobiosyl, β-D-glucopyranosyl, β-D-galactopyranosyl, β-D-2-acetamido-2-deoxy-glucopyranosyl, β-D-fucopyranosyl, β-D-maltosyl, β-D-lactosyl, β-D-cellotriosyl and β-D-maltotriosyl;

R² is selected from:
- a) —C$_1$–C$_8$-alkyl, —C$_3$–C$_8$ alkenyl or —C$_3$–C$_7$-cycloalkyl unsubstituted or wherein each may be substituted with one to three substituents selected from: halogen, —O—C$_1$–C$_4$ alkyl, aryl, heteroaryl, O-aryl and O—heteroaryl,
- b) aryl,
- c) —CH$_2$OC(O)NH—R³,
- d) —CH$_2$O(CO)NH—SO$_2$—R³,
- e) —CH$_2$OC(O)—R³,
- f) —OR³,
- g) —OC(O)NH—R³,
- h) —O(CO)NH—SO$_2$—R³,
- i) —OC(O)—R³,
- j) —CH$_2$—NR³R⁴,
- k) —CH$_2$NHC(O)R³,
- l) —CH$_2$NHC(O)OR³,
- m) —CH$_2$NHC(O)NHR³,
- n) —NR³R⁴,
- o) —NHC(O)R³,
- p) —NHC(O)OR³,
- q) —NHC(O)NHR³,
- r) —C(O)R³,
- s) —CO$_2$-t-Bu,
- t) —CONR³R⁴,
- u) —CH=CR³R⁴,
- v) 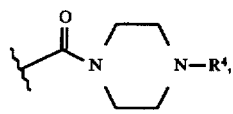
- w) 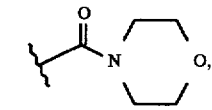
- x) 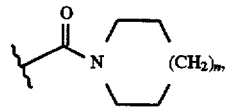

n = 0, 1, 2, 3, and y)

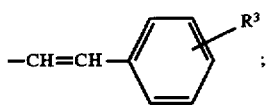

$R^3$ and $R^4$ are independently selected from:
a) —H,
b) $C_1$–$C_{10}$-alkyl, $C_3$–$C_{10}$ alkenyl or $C_3$–$C_{10}$-cycloalkyl, unsubstituted or wherein each may be substituted with one to three substituents selected from:
1) halogen
2) —O—$C_1$–$C_4$ alkyl,
3) aryl,
4) heteroaryl,
5) =O,
6) —C(O)-aryl,
7) —C(O)—$C_1$–$C_{10}$ alkyl,
8) —C(O)O-aryl,
9) —C(O)O—$C_1$–$C_{10}$ alkyl,
10) —C(O)NH-aryl,
11) —C(O)NH—$C_1$–$C_{10}$alkyl,
12) —N($R^5$)$_2$, wherein $R^5$ is independently selected at each occurrence from the group: —H, —$C_1$–$C_{10}$alkyl, —$C_3$–$C_{10}$ alkenyl, —$C_3$–$C_{10}$ cycloalkyl, aryl and heteroaryl;

c) aryl
$R^{3a}$ is selected from:
a) $C_{1–C10}$-alkyl, $C_3$–$C_{10}$ alkenyl or $C_3$–$C_{10}$-cycloalkyl, unsubstituted or wherein each may be substituted with one to three substituents selected from:
1) halogen
2) —O—$C_1$–$C_4$ alkyl,
3) aryl,
4) heteroaryl,
5) =O,
6) —C(O)-aryl,
7) —C(O)—$C_1$–$C_{10}$ alkyl,
8) —COO-aryl,
9) —COO—$C_1$–$C_{10}$ alkyl,
10) —C(O)NH-aryl,
11) —C(O)NH—$C_1$–$C_{10}$alkyl,
12) —N($R^5$)$_2$, wherein $R^5$ is independently at each occurrence from the group: —H, —$C_1$–$C_{10}$alkyl, -$C_3$–$C_{10}$ alkenyl, —$C_3$–$C_{10}$ cycloalkyl, aryl and heteroaryl;

b) aryl
$R^6$ and $R^7$ are independently selected from:
a) —H,
b) OH,
c) oxo (=O),
d) =N—$OR^3$,
e) —$NR^3R^4$,
f) —NHCOR$^{3a}$,
g) —NHCONR$^3R^4$,
h) —NHCO$_2$R$^{3a}$, and
i) —SO$_2$R$^{3a}$;
$R^8$ is selected from:

a) —H and
b) oxo (=O);

the line "- - -" designated as a represents a single or double bond when $R^6$ and $R^7$ are independently selected from —H and —SO$_2$R$^3$; otherwise, a is a single bond;

aryl is phenyl or bi-phenyl unsubstituted or wherein each may be substituted with one or two substituents selected from the group: halogen (F, Cl, Br, I), OH, NR$^3$R$^4$, CO$_2$R$^3$, $C_1$–$C_4$ alkyl, $C_1$–$C_4$ alkoxy, NO$_2$, CF$_3$, $C_1$–$C_4$ alkylthio, methylenedioxy, SO$_2$—($C_1$–$C_8$) alkyl, SO$_2$-aryl, and SO$_2$-heteroaryl; and heteroaryl is selected from
(a) an unsubstituted, monosubstituted or disubstituted five or six membered aromatic ring which consists of carbon atoms and from one to three heteroatoms selected from the group O, N and S,
(b) an unsubstituted, monosubstituted or disubstituted eight to ten membered bicyclic ring system which is completely or partially unsaturated and which consists of carbon atoms and from one to three heteroatoms selected from the group O, N, S, and NH;

and wherein the substituents on the heteroaryl are independently selected from the group consisting of halogen, OH, NR$^3$R$^4$, CO$_2$R$^3$, $C_1$–$C_4$ alkyl, $C_1$–$C_4$ alkoxy, NO$_2$, CF$_3$, $C_1$–$C_4$ alkylthio, SO$_2$—($C_1$–$C_8$) alkyl, SO$_2$-aryl, and SO$_2$-heteroaryl.

2. The compound of claim 1 wherein X is β-D-cellobiosyl.

3. The compound of claim 2 wherein $R^1$ is β-D-O-cellobiosyl.

4. The compound of claim 3 wherein $R^3$ is —H and $R^4$ is selected from phenyl; phenyl monosubstituted with halogen; benzyl; and $C_1$–$C_8$ alkyl.

5. The compound of claim 1 wherein $R^2$ is selected from
a) —CH=CR$^3$R$^4$,
b) —CH$_2$OC(O)NH—R$^3$,
c) —OC(O)NH—R$^3$,
d) —CH$_2$NHC(O)NHR$^3$,
e) —NHC(O)NHR$^3$,
f) —CH$_2$NHC(O)R$^{3a}$,
g) —NHC(O)R$^{3a}$ and
h) —C(O)NHR$^3$.

6. The compound of claim 5 wherein $R^6$ is selected from =O and —SO$_2$R$^{3a}$; $R^7$ is —H; and $R^8$ is —H.

7. The compound of claim 6 wherein $R^3$ is selected from:
a) $C_1$–$C_8$ alkyl unsubstituted or substituted with one to three substituents selected from the group consisting of halogen, —OC$_1$–$C_4$ alkyl, aryl and heteroaryl, and
b) aryl.

8. The compound of claim 5 wherein $R^2$ is selected from:
a) —CH=CH—$C_1$–$C_8$ alkyl, and
b) —CH=CH—phenyl, wherein the phenyl is optionally substituted with $C_1$–$C_8$ alkyl; and $R^6$ is selected from =O and —SO$_2$R$^3$.

9. The compound of claim 8 wherein $R^6$ is =O; $R^7$ is —H; and $R^8$ is —H.

10. A compound of claim 1 having structural formula III

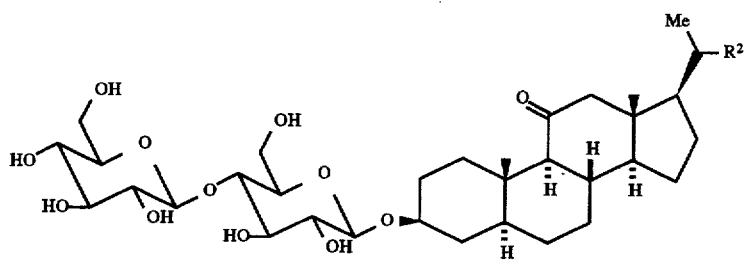
wherein R² is selected from:
a) 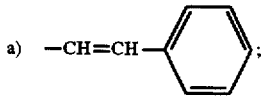
b) −CH=CH−CH(CH₃)−CH(CH₃)₂;
c) 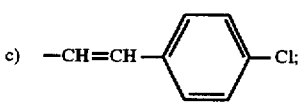
d) 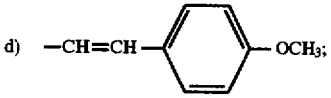
e) 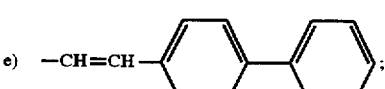
f) 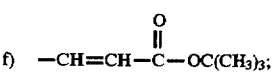
g) 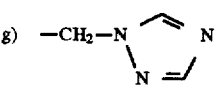
h) −CH₂CH₂CH(CH₃)CH(CH₃)₂;
i) 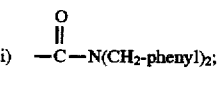
j) 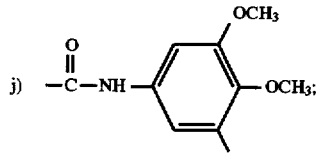
k) 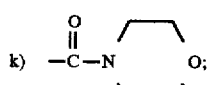
l) 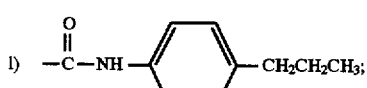
m) −C(=O)−N(n-C₅H₁₁)₂;
n) −CH₂OH;
o) 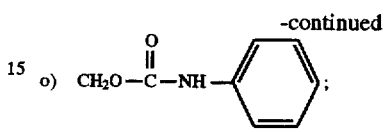
p) 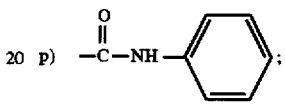
q) −CH₂O−C(=O)−NH(n-C₄H₉);
r) 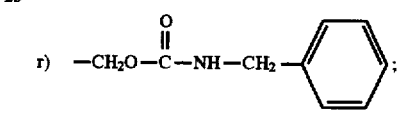
s) −CH₂O−C(=O)−NH−C(CH₃)₃;
t) 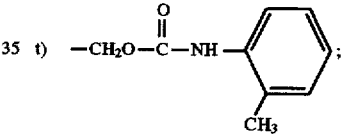
u) 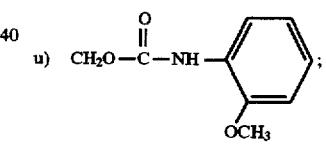
v) 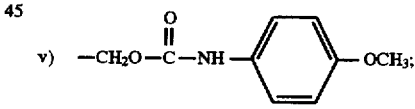
w) 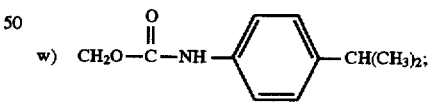
x) 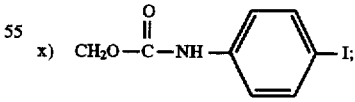
y) 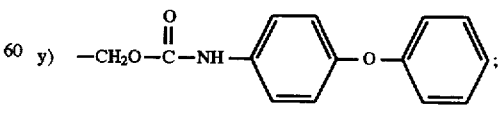
z) 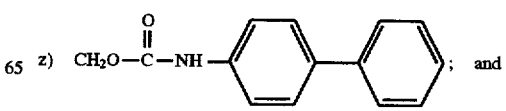; and aa) $-CH=CHCH(CH_3)CH(CH_3)_2$;

and the pharmaceutically acceptable salts and hydrates thereof.

11. The compound of claim 10 wherein $R^2$ is

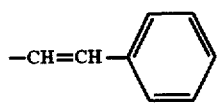

and the pharmaceutically acceptable salts and hydrates thereof.

12. A method of treating hypercholesterolemia comprising administering to a mammal in need of such treatment a therapeutically effective amount of a compound of claim 1.

13. A pharmaceutical composition comprising a therapeutically effective amount of a compound of claim 1 and a pharmaceutically acceptable carrier.

* * * * *